(12) United States Patent
Bourzat et al.

(10) Patent No.: US 6,548,533 B2
(45) Date of Patent: Apr. 15, 2003

(54) UREIDO SUBSTITUTED PYRROLIDINES

(75) Inventors: Jean-Dominique Bourzat, Vincennes (FR); Alain Commercon, Vitry-sur-Seine (FR); Bruno Jacques Christophe Filoche, Vitry-sur-Seine (FR)

(73) Assignee: Aventis Pharma Limited, West Malling (GB)

( * ) Notice: Subject to any disclaimer, the term of this patent is extended or adjusted under 35 U.S.C. 154(b) by 0 days.

(21) Appl. No.: 10/002,246

(22) Filed: Nov. 2, 2001

(65) Prior Publication Data

US 2002/0094994 A1 Jul. 18, 2002

Related U.S. Application Data

(63) Continuation of application No. PCT/GB00/01730, filed on May 5, 2000.
(60) Provisional application No. 60/176,191, filed on Jan. 14, 2000.

(30) Foreign Application Priority Data

May 5, 1999 (GB) .............................................. 9910419

(51) Int. Cl.[7] ..................... A61K 31/402; C07D 207/08
(52) U.S. Cl. ..................... 514/429; 514/423; 514/428; 548/530; 548/567
(58) Field of Search ................. 548/530, 567; 514/423, 428, 429

(56) References Cited

U.S. PATENT DOCUMENTS

2002/0065391 A1   5/2002   Stilz et al.

FOREIGN PATENT DOCUMENTS

| DE | 100 06 453 | | 8/2001 |
|---|---|---|---|
| DE | 10006453 | * | 8/2001 |
| EP | 0842945 | | 5/1998 |
| WO | WO99/54321 | | 10/1999 |
| WO | 99/54321 | * | 10/1999 |
| WO | WO01/58871 | | 8/2001 |

* cited by examiner

Primary Examiner—Alan L. Rotman
Assistant Examiner—Rita Desai
(74) Attorney, Agent, or Firm—Ronald G. Ort

(57) ABSTRACT

The invention is directed to physiologically active compounds of formula (I):

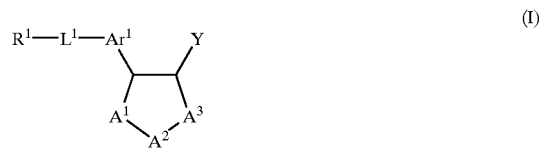

wherein one of $A^1$, $A^2$ and $A^3$ represents $NR^2$ and the others represent $C(R^3)(R^4)$; $R^1$ represents $R^5Z^1$—Het— or $R^6N(R^7)$—C(=O)—NH—$Ar^2$—; $Ar^1$ represents aryldiyl or heteroaryldiyl; $L^1$ represents a —$R^{12}$–$R^{13}$— linkage (where $R^{12}$ is a direct bond or an alkylene chain, an alkenylene chain or an alkynylene chain and $R^{13}$ is a direct bond, cycloalkylene, heterocycloalkylene, aryldiyl, heteroaryldiyl, —C(=$Z^3$)—$NR^{11}$—, —$NR^{11}$—C(=$Z^3$)—, —$Z^3$—, —C(=O)—, —C(=$NOR^{11}$)—, —$NR^{11}$—, —$NR^{11}$—C(=$Z^3$)—$NR^{11}$—, —$SO_2$—$NR^{11}$—, —NR —$SO_2$—, —O—C(=O)—, —C(=O)—O—, —$NR^{11}$—C(=O)—O— or —O—C(=O)—$NR^{11}$—); and their prodrugs, and pharmaceutically acceptable salts and solvates of such compounds and their prodrugs.

Such compounds have valuable pharmaceutical properties, in particular the ability to regulate the interaction of VCAM-1 and fibronectin with the integrin VLA-4 (α4β1).

33 Claims, No Drawings

UREIDO SUBSTITUTED PYRROLIDINES

This application is a continuation of PCT/GB00/01730, filed May 5, 2000, which claims priority from GB Application No. 9910419.2, filed May 5, 1999, and U.S. Provisional Application No. 60/176,191, filed Jan. 14, 2000; all these applications incorporated herein by reference.

This invention is directed to substituted pyrrolidines, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell—cell and cell-extracellular matrix interactions are mediated by protein ligands (e.g. fibronectin, VCAM-1 and vitronectin) and their integrin receptors [e.g. α5β1 (VLA-5), α4β1 (VLA-4) and αVβ3]. Recent studies have shown these interactions to play an important part in many physiological (e.g. embryonic development and wound healing) and pathological conditions (e.g. tumour-cell invasion and metastasis, inflanimation, atherosclerosis and autoimniune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called α and β. There are at least fifteen different α-subunits (α1-α9, α-L, α-M, α-X, α-IIb, α-V and α-E) and at least seven different β(β1-β7) subunits. The integrin family can be subdivided into classes based on the β subunits, which can be associated with one or more α-subunits. The most widely distributed integrins belong to the β1 class, also known as the very late antigens (VLA). The second class of integrins are leukocyte specific receptors and consist of one of three α-subunits (α-L, α-M or α-X) complexed with the β2 protein. The cytoadhesins α-IIbβ3 and α-Vβ3, constitute the third class of integrins.

The present invention principally relates to agents which modulate the interaction of the ligand VCAM-1 with its integrin receptor α4β1 (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin α4β1 mediates both cell—cell and cell-matrix interactions. Cells expressing α4β1 bind to the carboxy-terminal cell binding domain (CS-1) of the extra-cellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-γ, TNF-α, IL-1⊕ and IL-4.

Regulation of α4β1 mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which α4β1 binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflanimation (S. M. Wahl et al., J. Clin. Invest., 1994, 94, pages 655–662). In the oxazalone-sensitised model of inflammation (contact hypersensitivity response) in mice, intravenous administration of anti-α4 specific monoclonal antibodies significantly inhibited (50–60% reduction in the ear swelling response) the efferent response (P. L. Chisholm et al. J. Immunol., 1993, 23, pages 682–688). In a sheep model of allergic bronchoconstriction, HP1/2, an anti-α4 monoclonal antibody given intravenously or by aerosol, blocked the late response and the development of airway hyperresponsiveness (W. M. Abraham et al. J. Clin. Invest., 1994, 93 pages 776–787).

We have now found a novel group of substituted pyrrolidines which have valuable pharmaceutical properties, in particular the ability to regulate the interaction of VCAM-1 and fibronectin with the integrin VLA-4 ((α4β1).

Thus, in one aspect, the present invention is directed to compounds of general formula (I):

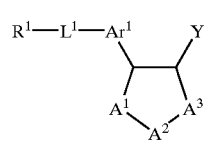

(I)

wherein:
one of $A^1, A^2$ and $A^3$ represents $NR^2$ and the others represent $C(R^3)(R^4)$;
$R^1$ represents $R^5Z^1$—Het— or $R^6N(R^7)$—C(=O)—NH—$Ar^2$—
$R^2$ represents —C(=O)—$R^8$, —C(=O)—$OR^{8a}$ or $R^{8b}$;
$R^3$ and $R^4$ each represent hydrogen or $R^8$;
$R^5$ represents aryl; heteroaryl; alkyl, alkenyl or alkynyl, each optionally substituted by $R^9$, —$Z^2R^{10}$, —$Z^3H$, —C(=O)—$R^{10}$, —$NR^{11}$—C(=$Z^3$)—$R^{11}$, —$NR^{11}$—C(=O)—$OR^{10}$, —$NR^{11}$—$SO_2$—$R^{10}$, —$SO_2$—$NY^1Y^2$, —$NY^1Y^2$ or —C(=$Z^3$)—$NY^1Y^2$; or cycloalkyl or heterocycloalkyl, each optionally substituted by $R^{10}$, —$Z^2R^{10}$, —$Z^3H$, —C(=O)—$R^{10}$, —$NR^{11}$—C(=$Z^3$)—$R^{10}$, —$NR^{11}$—C(=O)—$OR^{10}$, —$NR^{11}$—$SO_2$—$R^{10}$, —$SO_2$—$NY^1Y^2$, —$NY^1Y^2$ or —C(=$Z^3$)—$NY^1Y^2$;
$R^6$ represents hydrogen or lower alkyl and $R^7$ represents aryl, arylalkyl, heteroaryl or heteroarylalkyl; or
$R^6$ and $R^7$ together with the nitrogen atom to which they are attached form a cyclic amine;
$R^8$ represents alkyl, aryl, arylalkyl, cycloalkyl, cycloalkylalkyl, heteroaryl, heteroarylalkyl, heterocycloalkyl or heterocycloalkylalkyl, or alkyl substituted by an acidic functional group or corresponding protected derivative, or by —$Z^3$H, —$Z^2R^{10}$, —C(=O)—$NY^1Y^2$ or —$NY^1Y^2$;

$R^{8a}$ represents alkyl, aryl, arylalkyl, heteroaryl or heteroarylalkyl;

$R^{8b}$ represents alkyl, aryl, arylalkyl, heteroaryl, heteroarylalkyl or alkyl substituted by an acidic functional group or corresponding protected derivative;

$R^9$ represents aryl, cycloalkyl, cycloalkenyl, heteroaryl, or heterocycloalkyl;

$R^{10}$ represents alkyl, alkenyl, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl or heterocycloalkylalkyl;

$R^{11}$ represents hydrogen or lower alkyl;

$R^{12}$ is a direct bond or an alkylene chain, an alkenylene chain or an alkynylene chain;

$R^{13}$ is a direct bond, cycloalkylene, heterocycloalkylene, aryldiyl, heteroaryldiyl, —C(=$Z^3$)—$NR^{11}$—, —$NR^{11}$—C(=$Z^3$)—, —$Z^3$—, —C(=O)—, —C(=$NOR^{11}$), —$NR^{11}$—, —$NR^{11}$—C(=$Z^3$)—$NR^{11}$—, —$SO_2$—$NR^{11}$—, —$NR^{11}$—$SO_2$—, —O—C(=O)—, —C(=O)—O—, —$NR^{11}$—C(=O)—O— or —O—C(=O)—$NR^{11}$—;

$Ar^1$ represents aryldiyl or heteroaryldiyl;

$Ar^2$ represents aryldiyl or heteroaryldiyl;

Het represents a saturated, partially saturated or fully unsaturated 8 to 10 membered bicyclic ring system containing at least one heteroatom selected from O, S or N, optionally substituted by one or more aryl group substituents;

$L^1$ represents a —$R^{12}$—$R^{13}$— linkage;

Y is carboxy or an acid bioisostere;

$Y^1$ and $Y^2$ are independently hydrogen, alkenyl, alkyl, aryl, arylalkyl, cycloalkyl, heteroaryl or heteroarylalkyl; or the group —$NY^1Y^2$ may form a cyclic amine;

$Z^1$ represents NH;

$Z^2$ is O or $S(O)_n$;

$Z^3$ is O or S;

n is zero or an integer 1 or 2;

(but excluding compounds where an oxygen, nitrogen or sulphur atom is attached directly to a carbon carbon multiple bond of an alkenyl or alkynyl residue);

and their prodrugs, and pharmaceutically acceptable salts and solvates (e.g. hydrates) of such compounds and their prodrugs.

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986,21,p283 "Bioisosterism In Drug Design"; Yun, Hwahak Sekye, 1993,33,p576–579 "Application Of Bioisosterism To New Drug Design"; Zhao, Huaxue Tongbao, 1995,p34–38 "Bioisosteric Replacement And Development Of Lead Compounds In Drug Design"; Graham, Theochem, 1995,343,p105–109 "Theoretical Studies Applied To Drug Design:ab initio Electronic Distributions In Bioisosteres"). Examples of suitable acid bioisosteres include: —C(=O)—NHOH, —C(=O)—$CH_2OH$, —C(=O)—$CH_2SH$, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acidic functional group" means a group with an acidic hydrogen within it. The "corresponding protected derivatives" are those where the acidic hydrogen atom has been replaced with a suitable protecting group. For suitable protecting groups see T. W. Green and P. G. M. Wuts in "Protective Groups in Organic Chemistry" John Wiley and Sons, 1991. Exemplary acidic functional groups include carboxyl (and acid bioisosteres), hydroxy, mercapto and imidazole. Exemplary protected derivatives include esters of carboxy groups, ethers of hydroxy groups, thioethers of mercapto groups and N-benzyl derivatives of imidazoles.

"Acyl" means an H—CO— or alkyl—CO— group in which the alkyl group is as described herein.

"Acylamino" is an acyl-NH— group wherein acyl is as defined herein.

"Alkenyl" means an aliphatic hydrocarbon group containing a carbon—carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched $C_{2-6}$alkenyl group. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by one or more halogen atoms. Particular alkyl groups have from 1 to about 6 carbon atoms. "Lower alkyl" as a group or part of a lower alkoxy group means unless otherwise specified, an aliphatic hydrocarbon group which may be straight or branched having about 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched $C_{1-6}$alkyl group. Exemplary alkylene radicals include methylene, ethylene and trimethylene.

"Alkylenedioxy" means an —O-alkyl-O— group in which the alkyl group is as defined above. Exemplary alkylenedioxy groups include methylenedioxy and ethylenedioxy.

"Alkylsulphinyl" means an alkyl-SO— group in which the alkyl group is as previously described. Preferred alkylsulphinyl groups are those in which the alkyl group is $C_{1-4}$alkyl.

"Alkylsulphonyl" means an alkyl-$SO_2$— group in which the alkyl group is as previously described. Preferred alkylsulphonyl groups are those in which the alkyl group is $C_{1-4}$alkyl.

"Alkylsulphonylcarbamoyl" means an alkyl-$SO_2$—NH—C(=O)— group in which the alkyl group is as previously described. Preferred alkylsulphonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon—carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a $C_{2-6}$alkynyl group. Exemplary alkenylene radicals include ethynylene and propynylene.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^1Y^2N$—, $Y^1Y^2NCO$—, $Y^1Y^2NSO_2$—, $Y^1Y^2N$—$C_{2-6}$alkylene-Z— [where Z is O, $NR^{11}$ or $S(O)_n$], alkylC(=O)—$Y^1N$—, alkyl$SO_2$—$Y^1N$— or alkyl optionally substituted with aryl, heteroaryl, hydroxy, or $Y^1Y^2N$—. When $R^5$ is an optionally substituted aryl group, this may particularly represent optionally substituted phenyl.

"Arylalkenyl" means an aryl-alkenyl-group in which the aryl and alkenyl moieties are as previously described.

"Arylalkyl" means an aryl-alkyl-group in which the aryl and alkyl moieties are as previously described. Preferred arylalkyl groups contain a $C_{1-4}$ alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl-group in which the aryl and alkynyl moieties are as previously described.

"Aryldiyl" means an optionally substituted bivalent radical derived from an aryl group. Exemplary aryldiyl groups include optionally substituted phenylene, naphthylene and indanylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—CO— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$SO_2$— group in which the aryl group is as previously described.

"Arylsulphonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulphur, or nitrogen. Examples of azaheteroaryl groups include pyridyl, pyrimidinyl, quinolinyl, isoquinolinyl, quinazolinyl, imidazolyl, oxazolyl and benzimidazolyl.

"Azaheteroaryldiyl" means a bivalent radical derived from an azaheteroaryl group.

"Cyclic amine" means a 3 to 8 membered monocyclic cycloalkyl ring system where one of the ring carbon atoms is replaced by nitrogen and which (i) may be optionally substituted with one or more substituents selected from alkoxy, carboxamido, carboxy, hydroxy, oxo (or a 5-, 6- or 7-membered cyclic acetal derivative thereof) or $R^8$; (ii) may also contain a further heteroatom selected from O, S, $SO_2$, or $NY^3$ (where $Y^3$ is hydrogen, alkyl, aryl, arylalkyl, —C(=O)—$R^{14}$, —C(=O)—$OR^{14}$ or —$SO_2R^{14}$ and $R^{14}$ is alkyl, aryl, arylalkyl, cycloalkyl, cycloalkylalkyl, heteroaryl, heteroarylalkyl, heterocycloalkyl or heterocycloalkylalkyl); and (iii) may be fused to additional aryl (e.g. phenyl), heteroaryl (e.g. pyridyl), heterocycloalkyl or cycloalkyl rings to form a bicyclic or tricyclic ring system. Exemplary cyclic amines include pyrrolidine, piperidine, morpholine, piperazine, indoline, pyrindoline, tetrahydroquinolinyl and the like groups. When the group $R^6N(R^7)$— is a cyclic amine this may particularly represent indolinyl or tetrahydroquinolinyl.

"Cycloalkenyl" means a non-aromatic monocyclic or multicyclic ring system containing at least one carbon—carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl-group in which the cycloalkenyl and alkyl moieties are as previously described.

"Cycloalkylalkenyl" means a cycloalkyl-alkenyl-group in which the cycloalkyl and alkenyl moieties are as previously described.

"Cycloalkyl" means a saturated monocyclic or bicyclic ring system of about 3 to about 10 carbon atoms optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkyl" means a cycloalkyl-alkyl-group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylalkenyl" means a cycloalkyl-alkenyl-group in which the cycloalkyl and alkenyl moieties are as previously described.

"Cycloalkylalkyflyl" means a cycloalkyl-alkynyl-group in which the cycloalkyl and alkynyl moieties are as previously described.

"Cycloalkylene" means a bivalent radical derived from a cycloalkyl group. Exemplary cycloalkylene radicals include cyclopentylene and cyclohexylene.

"Halo" or "halogen" means fluoro, chloro, bromo, or iodo. Preferred are fluoro or chloro.

"Heteroaroyl" means a heteroaryl-CO— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzthiazolyl, furyl, imidazolyl, indolyl, indolizinyl, isoxazolyl, isoquinolinyl, isothiazolyl, oxazolyl, oxadiazolyl, pyrazinyl, pyridazinyl, pyrazolyl, pyridyl, pyrimidinyl, pyrrolyl, quinazolnyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above.

"Heteroarylalkenyl" means a heteroaryl-alkenyl-group in which the heteroaryl and alkenyl moieties are as previously described.

"Heteroarylalkynyl" means a heteroaryl-alkynyl-group in which the heteroaryl and alkynyl moieties are as previously described.

"Heteroarylalkyl" means a heteroaryl-alkyl-group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroaryldiyl" means a bivalent radical derived from a heteroaryl group.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-$SO_2$—NH—C(=O)— group in which the heteroaryl group is as previously described.

"Heterocycloalkyl" means: (i) a cycloalkyl group of about 3 to 7 ring members which contains one or more heteroatoms selected from O, S or $NY^3$ and optionally substituted by oxo; (ii) an partially saturated multicyclic heterocarbocyclic moiety in which an aryl (or heteroaryl ring), each optionally substituted by one or more "aryl group substituents", and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Heterocycloalkylene" means a bivalent radical derived from a heterocycloalkyl group.

"Hydroxyalkyl" means a HO-alkyl-group in which alkyl is as previously defined. Preferred hydroxyalkyl groups contain $C_{1-4}$alkyl for example hydroxymethyl and 2-hydroxyethyl.

"Phenylene" means an optionally substituted bivalent radical derived from a phenyl group. Suitable substituents include one or more "aryl group substituents" as defined above, particularly halogen, methyl or methoxy.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates.

Suitable esters of compounds of formula (I) containing a carboxy group, are for example those described by F. J. Leinweber, Drug Metab. Res., 1987, 18, page 379.

An especially useful class of esters of compounds of formula (I) containing a hydroxy group, may be formed from acid moieties selected from those described by Bundgaard et. al., J. Med. Chem., 1989, 32 , page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, omithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent a group $R^5Z^1$—Het— in which $R^5$ is optionally substituted aryl (especially optionally substituted phenyl), optionally substituted heteroaryl, arylalkyl (e.g. benzyl and phenethyl) or cycloalkyl (e.g. cyclohexyl), $Z^1$ is NH and Het is an 8 to 10 membered bicyclic system

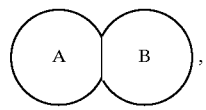

wherein ring

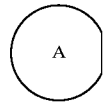

is a 5 or 6 membered heteroaryl ring and ring

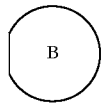

is a 5 or 6 membered heteroaryl or a benzene ring, each ring optionally substituted by one or more "aryl group substituents" as defined above, and the two rings are joined together by a carbon—carbon linkage or a carbon-nitrogen linkage.

Ring

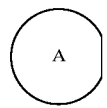

may particularly represent a 5 membered heteroaryl ring (especially a 5 membered azaheteroaryl ring), optionally substituted by one or more "aryl group substituents" as defined above.

Ring

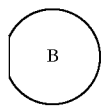

may particularly represent a benzene ring, optionally substituted by one or more "aryl group substituents" as defined above.

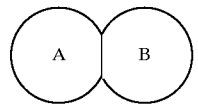

may particularly represent a 9 membered bicyclic system in which rings

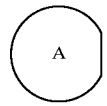 and 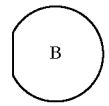

are as defined just above and the two rings are joined together by carbon atom linkages.

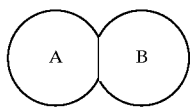

is preferably optionally substituted benzoxazolyl or optionally substituted benzimidazolyl, each (more particularly ring

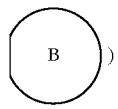

)

optionally substituted by one or more "aryl group substituents" as defined above [examples of particular aryl group substituents include lower alkyl (e.g. methyl), lower alkoxy (e.g. methoxy), amino, halogen, hydroxy, lower alkylthio, lower alkylsulphinyl, lower alkylsulphonyl, nitro or trifluoromethyl].

$R^1$ may also particularly represent a group $R^6N(R^7)$—C(=O)—NH—$Ar^2$— in which $R^6$ is $C_{1-4}$alkyl (e.g. methyl or ethyl, especially methyl), $R^7$ is aryl (especially an optionally substituted phenyl, where the optional substituent is an "aryl group substituent" as defined above) and $Ar^2$ is (i) optionally substituted phenylene, such as optionally substituted m- or p-phenylene, preferably optionally substituted p-phenylene, more preferably a 3-substituted p-phenylene (preferred optional substituents include $C_{1-4}$ alkyl, $C_{1-4}$ alkoxy, $C_{1-4}$alkylthio, $C_{1-4}$alkylsulphinyl and $C_{1-4}$alkylsulphonyl, especially methyl, methoxy, methylthio, methylsulphinyl and methylsulphonyl) or (ii) optionally substituted azaheteroaryldiyl, such as optionally substituted pyridinediyl, preferably a p-pyridinediyl, where the optional substituents include $C_{1-4}$ alkyl and $C_{1-4}$alkoxy, especially methyl and methoxy, more preferably a pyridine-2,5-diyl which is substituted in the 4- or 6-position with a methyl or methoxy group. $Ar^2$ is preferably optionally substituted phenylene (e.g. p-phenylene), especially where the substituent is $C_{1-4}$ alkyl or $C_{1-4}$ alkoxy.

$R^1$ may also particularly represent a group $R^6N(R^7)$—C(=O)—NH—$Ar^2$— in which $R^6$ is $C_{1-4}$alkyl (e.g. methyl or ethyl, especially methyl), $R^7$ is arylalkyl, especially aryl-$CH_2$— or aryl-$CH(CH_3)$—, preferably optionally substituted benzyl or optionally substituted 1-phenylethyl, where the optional substituent is an "aryl group substituent" as defined above and $Ar^2$ is (i) optionally substituted phenylene, such as optionally substituted m- or p-phenylene, preferably optionally substituted p-phenylene, more preferably a 3-substituted p-phenylene (preferred optional substituents include $C_{1-4}$alkyl, $C_{1-4}$alkoxy, $C_{1-4}$alkylthio, $C_{1-4}$alkylsulphinyl and $C_{1-4}$alkylsulphonyl, especially methyl, methoxy, methylthio, methylsulphinyl and methylsulphonyl) or (ii) optionally substituted azaheteroaryldiyl, such as optionally substituted pyridinediyl, preferably a p-pyridinediyl, where the optional substituents include $C_{1-4}$alkyl and $C_{1-4}$alkoxy, especially methyl and methoxy, more preferably a pyridine-2,5-diyl which is substituted in the 4- or 6-position with a methyl or methoxy group.

$R^1$ may also particularly represent a group $R^6N(R^7)$—C(=O)—NH—$Ar^2$— in which $R^6N(R^7)$— is a bicyclic amine containing 9–10 atoms, especially indolinyl or tetrahydroquinolinyl and $Ar^2$ is (i) optionally substituted phenylene, such as optionally substituted m- or p-phenylene, preferably optionally substituted p-phenylene, more preferably a 3-substituted p-phenylene (preferred optional substituents include $C_{1-4}$alkyl, $C_{1-4}$alkoxy, $C_{1-4}$alkylthio, $C_{1-4}$alkylsulphinyl and $C_{1-4}$alkylsulphonyl, especially methyl, methoxy, methylthio, methylsulphinyl and methylsulphonyl) or (ii) optionally substituted azaheteroaryldiyl, such as optionally substituted pyridinediyl, preferably a p-pyridinediyl, where the optional substituents include $C_{1-4}$alkyl and $C_{1-4}$alkoxy, especially methyl and methoxy, more preferably a pyridine-2,5-diyl which is substituted in the 4- or 6-position with a methyl or methoxy group.

$R^1$ may also particularly represent a group $R^6N(R^7)$—C(=O)—NH—$Ar^2$— in which $R^6$ is hydrogen, $R^7$ is (i) aryl, especially optionally substituted phenyl, where the optional substituent is an "aryl group substituent" as defined above or (ii) optionally substituted pyridyl, especially optionally substituted 2-pyridyl (preferred optional substituents include $C_{1-4}$alkyl and $C_{1-4}$alkoxy, especially methyl and methoxy) and $Ar^2$ is (i) optionally substituted phenylene, such as optionally substituted m- or p-phenylene, preferably optionally substituted p-phenylene, more preferably a 3-substituted p-phenylene (preferred optional substituents include $C_{1-4}$alkyl, $C_{1-4}$alkoxy, $C_{1-4}$alkylthio, $C_{1-4}$alkylsulphinyl and $C_{1-4}$alkylsulphonyl, especially methyl, methoxy, methylthio, methylsulphinyl and methylsulphonyl) or (ii) optionally substituted azaheteroaryldiyl, such as optionally substituted pyridinediyl, preferably a p-pyridinediyl, where the optional substituents include $C_{1-4}$alkyl and $C_{1-4}$alkoxy, especially methyl and methoxy, more preferably a pyridine-2,5-diyl which is substituted in the 4- or 6-position with a methyl or methoxy group. $R^7$ is particularly phenyl or ortho substituted phenyl [preferred substituents include $C_{1-4}$alkoxy (e.g. methoxy) or especially $C_{1-4}$alkyl (e.g. methyl)]. $Ar^2$ is preferably optionally substituted phenylene (e.g. p-phenylene), especially where the substituent is $C_{1-4}$alkyl or $C_{1-4}$alkoxy.

$L^1$ may particularly represent a —$R^{12}$—$R^{13}$— linkage where $R^{12}$ represents a straight or branched $C_{1-6}$alkylene chain, especially a straight or branched $C_{1-4}$alkylene chain (e.g. methylene), and $R^{13}$ represents —C(=$Z^3$)—$NR^{11}$—, preferably —C(=O)—$NR^{11}$—, especially where $R^{11}$ is hydrogen or lower alkyl (e.g. methyl).

$Ar^1$ may particularly represent optionally substituted aryldiyl, especially optionally substituted m- or p-phenylene, more especially optionally substituted p-phenylene. Preferred substituents include $C_{1-4}$alkyl and $C_{1-4}$alkoxy, especially methyl and methoxy.

$Ar^1$ may also particularly represent optionally substituted azaheteroaryldiyl, especially optionally substituted pyridinediyl, more especially optionally substituted p-pyridinediyl. Preferred substituents include $C_{1-4}$alkyl and $C_{1-4}$alkoxy, especially methyl and methoxy.

$Ar^1$ is preferably unsubstituted p-phenylene.

One of $A^1$, $A^2$ and $A^3$ may particularly represent $NR^2$ (especially wherein $R^2$ is —C(=O)—$R^8$ or aryl$C_{1-4}$alkyl, e.g. benzyl) and the others represent $CH_2$. $R^8$ may preferably represent $C_{1-4}$alkyl or phenyl.

Y may particularly represent carboxy.

It is to be understood that this invention covers all appropriate combinations of the particular and preferred groupings referred to herein.

A particular group of compounds of the invention are compounds of formula (Ia):

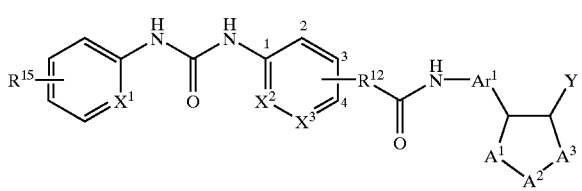

(Ia)

in which $A^1$, $A^2$, $A^3$, $R^{12}$, $Ar^1$ and Y are as hereinbefore defined, $R^{15}$ is hydrogen, halogen, lower alkyl or lower alkoxy, $X^1$ is $CR^{16}$ (where $R^{16}$ is hydrogen, lower alkyl or lower alkoxy), $X^2$ and $X^3$ independently represent N or $CR^{17}$ (where $R^{17}$ is hydrogen, amino, halogen, hydroxy, lower alkyl, lower alkoxy, lower alkylthio, lower alkylsulphinyl, lower alkylsulphonyl, nitro or trifluoromethyl), and the group containing $R^{12}$ is attached at the ring 3 or 4 position, and their prodrugs and pharmaceutically acceptable salts, and solvates (e.g. hydrates) of compounds of formula (Ia) and their prodrugs.

Compounds of formula (Ia) in which $R^{15}$ represents hydrogen are preferred.

Compounds of formula (Ia) in which $X^1$ represents $CR^{16}$ where $R^{16}$ is $C_{1-4}$alkyl (e.g. methyl) are preferred.

Compounds of formula (Ia) in which $X^2$ represents $CR^{17}$, especially where $R^{17}$ is $C_{1-4}$alkoxy (e.g. methoxy) are also preferred.

Compounds of formula (Ia) in which $X^3$ represents CH are also preferred.

Compounds of formula (Ia) in which $R^{12}$ represents a straight or branched $C_{1-6}$alkylene chain, especially a straight $C_{1-4}$alkylene chain, more especially methylene, are preferred.

Compounds of formula (Ia) in which $Ar^1$ represents an optionally substituted aryldiyl, especially optionally substituted m- or p-phenylene, more especially optionally substituted p-phenylene, are preferred. Preferred substituents include $C_{1-4}$alkyl and $C_{1-4}$alkoxy, especially methyl and methoxy.

Compounds of formula (Ia) in which $Ar^1$ represents optionally substituted azaheteroaryldiyl, especially optionally substituted pyridinediyl, more especially optionally substituted p-pyridinediyl are also preferred. Preferred substituents include $C_{1-4}$alkyl and $C_{1-4}$alkoxy, especially methyl and methoxy.

Compounds of formula (Ia) in which $Ar^1$ represents unsubstituted p-phenylene are particularly preferred.

Compounds of formula (Ia) in which one of $A^1$, $A^2$ and $A^3$ represents $NR^2$ [especially where $R^2$ is —C(=O)—$R^8$ or aryl$C_{1-4}$alkyl] and the others represent $CH_2$ are preferred.

Compounds of formula (Ia) in which Y represents carboxy are preferred.

The group containing $R^{12}$ may preferably be attached at the ring 4 position.

A preferred group of compounds of the invention are compounds of formula (Ia) in which:
$R^{15}$ is hydrogen; $X^1$ represents $CR^{16}$ (especially where $R^{16}$ is $C_{1-4}$alkyl, e.g. methyl); $X^2$ represent $CR^{17}$ (especially where $R^{17}$ is $C_{1-4}$alkoxy, e.g. methoxy); $X^3$ represents CH; $R^{12}$ is a straight $C_{1-4}$alkylene chain (especially methylene); $Ar^1$ is an optionally substituted phenylene (e.g. methyl or methoxy substituted p-phenylene, or especially unsubstituted p-phenylene,); one of $A^1$, $A^2$ and $A^3$ represents $NR^2$ (in which $R^2$ is —C(=O)—$R^8$ where $R^8$ is $C_{1-4}$alkyl or phenyl, or $R^2$ is aryl$C_{1-4}$alkyl, e.g. benzyl) and the others represent $CH_2$; Y represents carboxy; and the group containing $R^{12}$ is attached at the ring 4 position; and their prodrugs, and pharmaceutically acceptable salts and solvates (e.g. hydrates) of such compounds and their prodrugs.

Another particular group of compounds of the invention are compounds of formula (Ib):

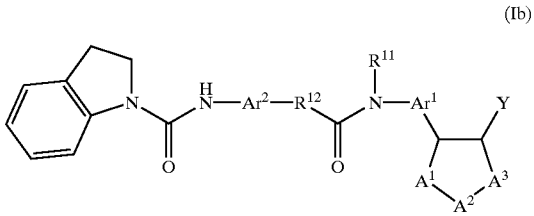

(Ib)

in which $R^{11}$, $R^{12}$, $Ar^1$, $Ar^2$, $A^1$, $A^2$, $A^3$ and Y are as hereinbefore defined, and their prodrugs and pharmaceutically acceptable salts, and solvates (e.g. hydrates) of compounds of formula (Ib) and their prodrugs.

Compounds of formula (Ib) in which $Ar^2$ represents optionally substituted aryldiyl, such as optionally substituted m- or p-phenylene, preferably optionally substituted p-phenylene, more preferably a 3-substituted p-phenylene (preferred optional substituents include $C_{1-4}$alkyl, $C_{1-4}$alkoxy, $C_{1-4}$alkylthio, $C_{1-4}$alkylsulphinyl and $C_{1-4}$alkylsulphonyl, especially methyl, methoxy, methylthio, methylsulphinyl and methylsulphonyl) are preferred.

Compounds of formula (Ib) in which $Ar^2$ represents optionally substituted azaheteroaryldiyl, such as optionally substituted pyridinediyl, preferably a p-pyridinediyl, where the optional substituents include $C_{1-4}$alkyl and $C_{1-4}$alkoxy, especially methyl and methoxy, more preferably a pyridine-2,5-diyl which is substituted in the 4- or 6-position with a methyl or methoxy group. are also preferred.

Compounds of formula (Ib) in which $R^{12}$ represents a straight or branched $C_{1-6}$alkylene chain, especially a straight or branched $C_{1-4}$alkylene chain, more especially methylene, are preferred.

Compounds of formula (Ib) in which $R^{11}$ represents hydrogen are preferred.

Compounds of formula (Ib) in which $R^{11}$ represents lower alkyl (e.g. methyl) are also preferred.

Compounds of formula (Ib) in which $Ar^1$ represents an optionally substituted aryldiyl, especially optionally substituted m- or p-phenylene, more especially optionally substituted p-phenylene, are preferred. Preferred substituents for $Ar^1$ include $C_{1-4}$alkyl and $C_{1-4}$alkoxy, especially methyl and methoxy.

Compounds of formula (Ib) in which $Ar^1$ represents optionally substituted azaheteroaryldiyl, especially optionally substituted pyridinediyl, more especially optionally substituted p-pyridinediyl are also preferred. Preferred substituents include $C_{1-4}$alkyl and $C_{1-4}$alkoxy, especially methyl and methoxy.

Compounds of formula (Ib) in which one of $A^1$, $A^2$ and $A^3$ represents $NR^2$ (especially wherein $R^2$ is —C(=O)—$R^8$ or aryl$C_{1-4}$alkyl) and the others represent $CH_2$ are preferred.

Compounds of formula (Ib) in which Y represents carboxy are preferred.

A preferred group of compounds of the invention are compounds of formula (Ib) in which:
$Ar^2$ is p-phenylene or substituted p-phenylene (especially 3-methyl-p-phenylene, 3-methoxy-p-phenylene, 3-methylthio-p-phenylene, 3-methylsulphinyl-p-phenylene and 3-methylsulphonyl-p-phenylene) or p-pyridinediyl or substituted p-pyridinediyl [especially 4(or 6)-methyl(or methoxy)-p-pyridine-2,5-diyl]; $R^{12}$ is a straight or branched $C_{1-4}$alkylene chain, (especially methylene); $R^{11}$ is hydrogen or lower alkyl (e.g. methyl); $Ar^1$ is an optionally substituted aryldiyl [especially p-phenylene, and methyl(or methoxy) substituted p-phenylene]; one of $A^1$, $A^2$ and $A^3$ represents $NR^2$ (in which $R^2$ is —C(=O)—$R^8$ where $R^8$ is $C_{1-4}$alkyl or phenyl, or $R^2$ is aryl$C_{1-4}$alkyl, e.g. benzyl) and the others represent $CH_2$; Y represents carboxy; and their prodrugs, and pharmaceutically acceptable salts and solvates (e.g. hydrates) of such compounds and their prodrugs.

Another particular group of compounds of the invention are compounds of formula (Ic):

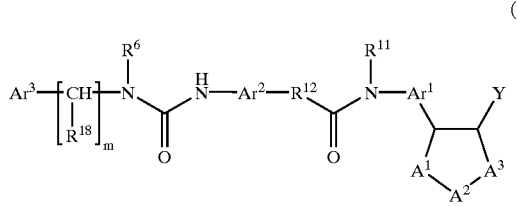

(Ic)

in which $R^{11}$, $R^{12}$, $Ar^1$, $Ar^2$, $A^1$, $A^2$, $A^3$ and Y are as hereinbefore defined, $R^6$ is lower alkyl, $R^{18}$ is hydrogen or methyl, $Ar^3$ is aryl and m is zero or 1, and their prodrugs and pharmaceutically acceptable salts, and solvates (e.g. hydrates) of compounds of formula (Ic) and their prodrugs.

Compounds of formula (Ic) in which $Ar^3$ represents phenyl, optionally substituted by an "aryl group substituent" as defined above, are preferred.

Compounds of formula (Ic) in which $R^6$ represents $C_{1-4}$alkyl, especially methyl or ethyl, are preferred.

Compounds of formula (Ic) in which $Ar^2$ represents optionally substituted aryldiyl, such as optionally substituted m- or p-phenylene, preferably optionally substituted p-phenylene, more preferably a 3-substituted p-phenylene (preferred optional substituents include $C_{1-4}$alkyl, $C_{1-4}$alkoxy, $C_{1-4}$alkylthio, $C_{1-4}$alkylsulphinyl and $C_{1-4}$alkylsulphonyl, especially methyl, methoxy, methylthio, methylsulphinyl and methylsulphonyl) are preferred.

Compounds of formula (Ic) in which $Ar^2$ represents optionally substituted azaheteroaryldiyl, such as optionally substituted pyridinediyl, preferably a p-pyridinediyl, where the optional substituents include $C_{1-4}$alkyl and $C_{1-4}$alkoxy, especially methyl and methoxy, more preferably a pyridine-2,5-diyl which is substituted in the 4- or 6-position with a methyl or methoxy group. are also preferred.

Compounds of formula (Ic) in which $R^{12}$ represents a straight or branched $C_{1-6}$alkylene chain, especially a straight or branched $C_{1-4}$alkylene chain, more especially methylene, are preferred.

Compounds of formula (Ic) in which $R^{11}$ represents hydrogen are preferred.

Compounds of formula (Ic) in which $R^{11}$ represents lower alkyl (e.g. methyl) are also preferred.

Compounds of formula (Ic) in which $Ar^1$ represents an optionally substituted aryldiyl, especially optionally substituted m- or p-phenylene, more especially optionally substituted p-phenylene, are preferred. Preferred substituents for $Ar^1$ include $C_{1-4}$alkyl and $C_{1-4}$alkoxy, especially methyl and methoxy.

Compounds of formula (Ic) in which $Ar^1$ represents optionally substituted azaheteroaryldiyl, especially optionally substituted pyridinediyl, more especially optionally substituted p-pyridinediyl are also preferred. Preferred substituents include $C_{1-4}$alkyl and $C_{1-4}$alkoxy, especially methyl and methoxy.

Compounds of formula (Ic) in which one of $A^1$, $A^2$ and $A^3$ represents $NR^2$ (especially wherein $R^2$ is —C(=O)—$R^8$ or aryl$C_{1-4}$alkyl) and the others represent $CH_2$, are preferred.

Compounds of formula (Ic) in which Y represents carboxy are preferred.

A preferred group of compounds of the invention are compounds of formula (Ic) in which:
$Ar^3$ is phenyl; $R^{18}$ is hydrogen or methyl; m is zero or one; $R^6$ is $C_{1-4}$alkyl (especially methyl or ethyl); $Ar^2$ is p-phenylene or optionally substituted p-phenylene (especially 3-methyl-p-phenylene, 3-methoxy-p-phenylene, 3-methylthio-p-phenylene, 3-methylsulphinyl-p-phenylene and 3-methylsulphonyl-p-phenylene) or p-pyridinediyl or substituted p-pyridinediyl [especially 4(or 6)-methyl(or methoxy)-p-pyridine-2,5-diyl]; $R^{12}$ is a straight or branched $C_{1-4}$alkylene chain, (especially methylene); $R^{11}$ is hydrogen or lower alkyl (e.g. methyl); $Ar^1$ is an optionally substituted phenylene [especially p-phenylene, and methyl(or methoxy) substituted p-phenylene]; one of $A^1$, $A^2$ and $A^3$ represents $NR^2$ (in which $R^2$ is —C(=O)—$R^8$ where $R^8$ is $C_{1-4}$alkyl or phenyl, or $R^2$ is aryl$C_{1-4}$alkyl, e.g. benzyl) and the others represent $CH_2$; Y is carboxy; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Id):

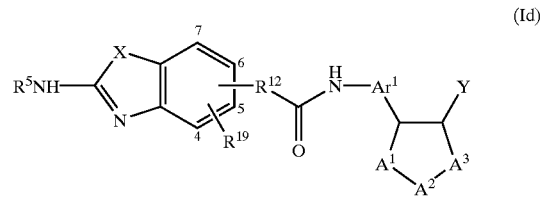

(Id)

in which $R^5$, $R^{12}$, $Ar^1$, $A^1$, $A^2$, $A^3$ and Y are as hereinbefore defined, X is NR or O (where R is H or lower alkyl), $R^{19}$ is hydrogen, $C_{1-4}$alkyl or $C_{1-4}$alkoxy, and their prodrugs and pharmaceutically acceptable salts, and solvates (e.g. hydrates) of compounds of formula (Id) and their prodrugs.

Compounds of formula (Id) in which $R^5$ represents optionally substituted aryl, especially optionally substituted phenyl, are preferred. Preferred optional substituents include lower alkyl (e.g. methyl), lower alkyl (e.g. methoxy), halo (e.g. fluoro) and $Y^1Y^2N$— (e.g. dimethylamino). $R^5$ especially represents ortho-tolyl.

Compounds of formula (Id) in which $R^{12}$ represents a straight or branched $C_{1-6}$alkylene chain, especially a straight $C_{1-4}$alkylene chain, more especially methylene, are preferred.

Compounds of formula (Id) in which $Ar^1$ represents an optionally substituted aryldiyl, especially optionally substituted m- or p-phenylene, more especially optionally substituted p-phenylene, are preferred. Preferred substituents for $Ar^1$ include $C_{1-4}$alkyl and $C_{1-4}$alkoxy, especially methyl and methoxy.

Compounds of formula (Id) in which $Ar^1$ represents optionally substituted azaheteroaryldiyl, especially optionally substituted pyridinediyl, more especially optionally substituted p-pyridinediyl are also preferred. Preferred substituents include $C_{1-4}$alkyl and $C_{1-4}$alkoxy, especially methyl and methoxy.

Compounds of formula (Id) in which $Ar^1$ represents unsubstituted p-phenylene are particularly preferred.

Compounds of formula (Id) in which one of $A^1$, $A^2$ and $A^3$ represents $NR^2$ (especially wherein $R^2$ is —C(=O)—$R^8$ or aryl$C_{1-4}$alkyl) and the others represent $CH_2$ are preferred.

Compounds of formula (Id) in which Y represents carboxy are preferred.

A preferred group of compounds of the invention are compounds of formula (Id) in which:

$R^5$ is optionally substituted phenyl (especially ortho-tolyl); X is O; $R^{12}$ is a straight $C_{1-4}$alkylene chain (especially methylene); $Ar^1$ is an optionally substituted phenylene (e.g. methyl or methoxy substituted p-phenylene, or especially unsubstituted p-phenylene); one of $A^1$, $A^2$ and $A^3$ represents $NR^2$ (in which $R^2$ is —C(=O)—$R^8$ where $R^8$ is $C_{1-4}$alkyl or phenyl, or $R^2$ is aryl$C_{1-4}$alkyl, e.g. benzyl) and the others represent $CH_2$; Y is carboxy; and the group containing $R^{12}$ is attached at the benzoxazole ring 6 position; and the corresponding N-oxides, and their prodrugs; and pharmaceutically acceptable salts and solvates (e.g. hydrates) of such compounds and their N-oxides and prodrugs.

Particular compounds of the invention are selected from the following:

1-benzyl-4-(4-{2-[3-methoxy-4-(3-o-tolyl-ureido)-phenyl]-acetylamino}-phenyl)-pyrrolidine-3-carboxylic acid;

1-acetyl-4-(4-{2-[3-methoxy-4-(3-o-tolyl-ureido)-phenyl]-acetylamino}-phenyl)-pyrrolidine-3-carboxylic acid;

1-acetyl-2-(4-{2-[3-methoxy-4-(3-o-tolyl-ureido)-phenyl]-acetylamino}-phenyl)-pyrrolidine-3-carboxylic acid;

1-benzoyl-4-(4-{2-[3-methoxy-4-(3-o-tolyl-ureido)-phenyl]-acetylamino}-phenyl)-pyrrolidine-3-carboxylic acid;

1-(3-carboxy-propionyl)4-(4-{2-[3-methoxy-4-(3-o-tolyl-ureido)-phenyl]-acetylamino}-phenyl)-pyrrolidine-3-carboxylic acid;

1-benzoyl-2-(4-{2-[3-methoxy-4-(3-o-tolyl-ureido)-phenyl]-acetylamino}-phenyl)-pyrrolidine-3-carboxylic acid;

1-acetyl-4-(4-{2-[4-(3-methyl-3-o-tolyl-ureido)-phenyl]-acetylamino}-phenyl)-pyrrolidine-3-carboxylic acid;

1-benzoyl-4-(4-{2-[4-(3-methyl-3-o-tolyl-ureido)-phenyl]-acetylamino}-phenyl)-pyrrolidine-3-carboxylic acid;

4-(4-{2-[3-methoxy-4-(3-o-tolyl-ureido)-phenyl]-acetylamino}-phenyl)-pyrrolidine-3-carboxylic acid;

4-(4-{2-[4-(3-methyl-3-o-tolyl-ureido)-phenyl]-acetylamino}-phenyl)-1-(thiophene-2-carbonyl)-pyrrolidine-3-carboxylic acid;

4-(4-{2-[4-(3-methyl-3-o-tolyl-ureido)-phenyl]-acetylamino}-phenyl)-1-(pyridine-4-carbonyl)-pyrrolidine-3-carboxylic acid;

4-(4-{2-[4-(3-methyl-3-o-tolyl-ureido)-phenyl]-acetylamino}-phenyl)-1-(morpholin-4-yl-acetyl)-pyrrolidine-3-carboxylic acid;

1-(5-methyl-isoxazole-3-carbonyl)-4-(4-{2-[4-(3-methyl-3-o-tolyl-ureido)-phenyl]-acetylamino}-phenyl)-pyrrolidine-3-carboxylic acid;

1-acetyl-4-[4-(methyl-{[4-(3-methyl-3-o-tolyl-ureido)-phenyl]-acetyl}-amino)-phenyl]-pyrrolidine-3-carboxylic acid;

1-benzoyl-4-[4-(methyl-{[4-(3-methyl-3-o-tolyl-ureido)-phenyl]-acetyl}-amino)-phenyl]-pyrrolidine-3-carboxylic acid;

4-[4-(methyl-{[4-(3-methyl-3-o-tolyl-ureido)-phenyl]-acetyl}-amino)-phenyl]-1-(thiophene-2-carbonyl)-pyrrolidine-3-carboxylic acid;

4-[4-(methyl-{[4-(3-methyl-3-o-tolyl-ureido)-phenyl]-acetyl}-amino)-phenyl]-1-(pyridine-4-carbonyl)-pyrrolidine-3-carboxylic acid;

4-[4-(methyl-{[4-(3-methyl-3-o-tolyl-ureido)-phenyl]-acetyl}-amino)-phenyl]-1-(morpholin-4-yl-acetyl)-pyrrolidine-3-carboxylic acid;

1-(5-methyl-isoxazole-3-carbonyl)4-{4-[methyl-({4-[3-methyl-3-(2-methyl-hexa-1,3,5-trienyl)-ureido]-phenyl}-acetyl)-amino]-phenyl}-pyrrolidine-3-carboxylic acid;

1-acetyl-4-[4-(2-{4-[(2,3-dihydro-indole-1-carbonyl)-amino]-phenyl}-acetylamino)-phenyl]-pyrrolidine-3-carboxylic acid;

1-benzoyl-4-[4-(2-{4-[(2,3-dihydro-indole-1-carbonyl)-amino]-phenyl}-acetylamino)-phenyl]-pyrrolidine-3-carboxylic acid;

4-[4-(2-{4-[(2,3-dihydro-indole-1-carbonyl)-amino]-phenyl}-acetylamino)-phenyl]-1-(thiophene-2-carbonyl)-pyrrolidine-3-carboxylic acid;

4-[4-(2-{4-[(2,3-dihydro-indole-1-carbonyl)-amino]-phenyl}-acetylamino)-phenyl]-1-(pyridine-4-carbonyl)-pyrrolidine-3-carboxylic acid;

4-[4-(2-{4-[(2,3-dihydro-indole-1-carbonyl)-amino]-phenyl}-acetylamino)-phenyl]-1-(morpholin-4-yl-acetyl)-pyrrolidine-3-carboxylic acid;

4-[4-(2-{4-[(2,3-dihydro-indole-1-carbonyl)-amino]-phenyl}-acetylamino)-phenyl]-1-(5-methyl-isoxazole-3-carbonyl)-pyrrolidine-3-carboxylic acid;

1-acetyl-4-[4-[({4-[(2,3-dihydro-indole-1-carbonyl)-amino]-phenyl}-acetyl)-methyl-amino]-phenyl}-pyrrolidine-3-carboxylic acid;

1-benzoyl-4-{4-[({4-[(2,3-dihydro-indole-1-carbonyl)-amino]-phenyl}-acetyl)-methyl-amino]-phenyl}-pyrrolidine-3-carboxylic acid;

4-{4-[({4-[(2,3-dihydro-indole-1-carbonyl)-amino]-phenyl}-acetyl)-methyl-amino]-phenyl}-1-(thiophene-2-carbonyl)-pyrrolidine-3-carboxylic acid;

4{4-[({4-[(2,3-dihydro-indole-1-carbonyl)-amino]-phenyl}-acetyl)-methyl-amino]-phenyl}-1-(pyridine-4-carbonyl)-pyrrolidine-3-carboxylic acid;

4-{4-[({4-[(2,3-dihydro-indole-1-carbonyl)-amino]-phenyl}-acetyl)-methyl-amino]-phenyl}-1-(morpholin-4-yl-acetyl)-pyrrolidine-3-carboxylic acid;

4-{4-[({4-[(2,3-dihydro-indole-1-carbonyl)-amino]-phenyl}-acetyl)-methyl-amino]-phenyl}-1-(5-methyl-isoxazole-3-carbonyl)-pyrrolidine-3-carboxylic acid;

1-acetyl-4-(4-{2-[3-methoxy-4-(3-methyl-3-o-tolyl-ureido)-phenyl]-acetylamino}-phenyl)-pyrrolidine-3-carboxylic acid;

1-benzoyl-4-(4-{2-[3-methoxy-4-(3-methyl-3-o-tolyl-ureido)-phenyl]-acetylamino}-phenyl)-pyrrolidine-3-carboxylic acid;

4-(4-{2-[3-methoxy-4-(3-methyl-3-o-tolyl-ureido)-phenyl]-acetylamino}-phenyl)-1-(thiophene-2-carbonyl)-pyrrolidine-3-carboxylic acid;

4-(4-{2-[3-methoxy-4-(3-methyl-3-o-tolyl-ureido)-phenyl]-acetylamino}-phenyl)-1-(pyridine-4-carbonyl)-pyrrolidine-3-carboxylic acid;

4-(4-{2-[3-methoxy-4-(3-methyl-3-o-tolyl-ureido)-phenyl]-acetylamino}-phenyl)-1-(morpholin-4-yl-acetyl)-pyrrolidine-3-carboxylic acid;

4-(4-{2-[3-methoxy-4-(3-methyl-3-o-tolyl-ureido)-phenyl]-acetylamino}-phenyl)-1-(5-methyl-isoxazole-3-carbonyl)-pyrrolidine-3-carboxylic acid;

1-acetyl-4-[4-({[3-methoxy-4-(3-methyl-3-o-tolyl-ureido)-phenyl]-acetyl}-methyl-amino)-phenyl]-pyrrolidine-3-carboxylic acid;

1-benzoyl-4-[4-({[3-methoxy-4-(3-methyl-3-o-tolyl-ureido)-phenyl]-acetyl}-methyl-amino)-phenyl]-pyrrolidine-3-carboxylic acid;

4-[4-({[3-methoxy-4-(3-methyl-3-o-tolyl-ureido)-phenyl]-acetyl}-methyl-amino)-phenyl]-1-(thiophene-2-carbonyl)-pyrrolidine-3-carboxylic acid;

4-[4-({[3-methoxy-4-(3-methyl-3-o-tolyl-ureido)-phenyl]-acetyl}-methyl-amino)-phenyl]-1-(pyridine-4-carbonyl)-pyrrolidine-3-carboxylic acid;

4-[4-({[3-methoxy-4-(3-methyl-3-o-tolyl-ureido)-phenyl]-acetyl}-methyl-amino)-phenyl]-1-(morpholin-4-yl-acetyl)-pyrrolidine-3-carboxylic acid;

4-[4-({[3-methoxy-4-(3-methyl-3-o-tolyl-ureido)-phenyl]-acetyl}-methyl-amino)-phenyl]-1-(5-methyl-isoxazole-3-carbonyl)-pyrrolidine-3-carboxylic acid;

1-acetyl-4-[4-(2-{4-[(2,3-dihydro-indole-1-carbonyl)-amino]-3-methoxy-phenyl}-acetylamino)-phenyl]-pyrrolidine-3-carboxylic acid;

1-benzoyl-4-[4-(2-{4-[(2,3-dihydro-indole-1-carbonyl)-amino]-3-methoxy-phenyl}-acetylamino)-phenyl]-pyrrolidine-3-carboxylic acid;

4-[4-(2-{4-[(2,3-dihydro-indole-1-carbonyl)-amino]-3-methoxy-phenyl}-acetylamino)-phenyl]-1-(thiophene-2-carbonyl)-pyirolidine-3-carboxylic acid;

4-[4-(2-{4-[(2,3-dihydro-indole-1-carbonyl)-amino]-3-methoxy-phenyl}-acetylamino)-phenyl]-1-(pyridine-4-carbonyl)-pyrrolidine-3-carboxylic acid;

4-[4-(2-{4-[(2,3-dihydro-indole-1-carbonyl)-amino]-3-methoxy-phenyl}-acetylamino)-phenyl]-1-(morpholin-4-yl-acetyl)-pyrrolidine-3-carboxylic acid;

4-[4-(2-{4-[(2,3-dihydro-indole-1-carbonyl)-amino]-3-methoxy-phenyl}-acetylamino)-phenyl]-1-(5-methyl-isoxazole-3-carbonyl)-pyrrolidine-3-carboxylic acid;

1-acetyl-4-[({4-[(2,3-dihydro-indole-1-carbonyl)-amino]-3-methoxy-phenyl}-acetyl)-methyl-amino]-phenyl}-pyrrolidine-3-carboxylic acid;

1-benzoyl-4-{4-[({4-[(2,3-dihydro-indole-1-carbonyl)-amino]-3-methoxy-phenyl}-acetyl)-methyl-amino]-phenyl}-pyrrolidine-3-carboxylic acid;

4-{4-[({4-[(2,3-dihydro-indole-1-carbonyl)-amino]-3-methoxy-phenyl}-acetyl)-methyl-amino]-phenyl}-1-(thiophene-2-carbonyl)-pyrrolidine-3-carboxylic acid;

4-{4-[({4-[(2,3-dihydro-indole-1-carbonyl)-amino]-3-methoxy-phenyl}-acetyl)-methyl-amino]-phenyl}-1-(pyridine-4-carbonyl)-pyrrolidine-3-carboxylic acid;

4-{4-[({4-[(2,3-dihydro-indole-1-carbonyl)-amino]-3-methoxy-phenyl}-acetyl)-methyl-amino]-phenyl}-1-(morpholin-4-yl-acetyl)-pyrrolidine-3-carboxylic acid;

4-{4-[({4-[(2,3-dihydro-indole-1-carbonyl)-amino]-3-methoxy-phenyl}-acetyl)-methyl-amino]-phenyl}-(5-methyl-isoxazole-3-carbonyl)-pyrolidine-3-carboxylic acid;

1-acetyl-4-{4-[2-(2-o-tolylamino-benzoxazol-6-yl)-acetylamino]-phenyl}-pyrrolidine-3-carboxylic acid;

1-benzoyl-4-{4-[2-(2-o-tolylamino-benzoxazol-6-yl)-acetylamino]-phenyl}-pyrrolidine-3-carboxylic acid;

1-(thiophene-2-carbonyl)4-{4-[2-(2-o-tolylamino-benzoxazol-6-yl)-acetylamino]-phenyl}-pyrrolidine-3-carboxylic acid;

1-(pyridine-4-carbonyl)4-{4-[2-(2-o-tolylamino-benzoxazol-6-yl)-acetylamino]-phenyl}-pyrrolidine-3-carboxylic acid;

1-(morpholin-4-yl-acetyl)-4-{4-[2-(2-o-tolylamino-benzoxazol-6-yl)-acetylamino]-phenyl}-pyrrolidine-3-carboxylic acid;

1-(5-methyl-2,5-dihydro-isoxazole-3-carbonyl)-4-{4-[2-(2-o-tolylamino-benzoxazol-6-yl)-acetylamino]-phenyl}-pyrrolidine-3-carboxylic acid;

1-acetyl-4-(4-{methyl-[(2-o-tolylamino-benzoxazol-6-yl)-acetyl]-amino}-phenyl)-pyrrolidine-3-carboxylic acid;

1-benzoyl-4-(4-{methyl-[(2-o-tolylamino-benzoxazol-6-yl)-acetyl]-amino}-phenyl)-pyrrolidine-3-carboxylic acid;

4-(4-{methyl-[(2-o-tolylamino-benzoxazol-6-yl)-acetyl]-amino}-phenyl)-1-(thiophene-2-carbonyl)-pyrrolidine-3-carboxylic acid;

4-(4-{methyl-[(2-o-tolylamino-benzoxazol-6-yl)-acetyl]-amino}-phenyl)-1-(pyridine-4-carbonyl)-pyrrolidine-3-carboxylic acid;

4-(4-{methyl-[(2-o-tolylamino-benzoxazol-6-yl)-acetyl]-amino}-phenyl)-1-(morpholin-4-yl-acetyl)-pyrrolidine-3-carboxylic acid;

1-(5-methyl-2,5-dihydro-isoxazole-3-carbonyl)-4-(4-{methyl-[(2-o-tolylamino-benzoxazol-6-yl)-acetyl]-amino}-phenyl)-pyrrolidine-3-carboxylic acid;

1-acetyl-4-(4-{2-[2-(2-methoxy-phenylamino)-benzoxazol-6-yl]-acetylamino}-phenyl)-pyrrolidine-3-carboxylic acid;

1-benzoyl-4-(4-{2-[2-(2-methoxy-phenylamino)-benzoxazol-6-yl]-acetylamnino}-phenyl)-pyrrolidine-3-carboxylic acid;

4-(4-{2-[2-(2-methoxy-phenylamino)-benzoxazol-6-yl]-acetylamino}-phenyl)-1-(thiophene-2-carbonyl)-pyrrolidine-3-carboxylic acid;

4-(4-{2-[2-(2-methoxy-phenylamino)-benzoxazol-6-yl]-acetylamino}-phenyl)-1-(pyridine-4-carbonyl)-pyrrolidine-3-carboxylic acid;

4-(4-{2-[2-(2-methoxy-phenylamino)-benzoxazol-6-yl]-acetylamino}-phenyl)-1-(morpholin-4-yl-acetyl)-pyrrolidine-3-carboxylic acid;

4-(4-{2-[2-(2-methoxy-phenylamino)-benzoxazol-6-yl]-acetylamino}-phenyl)-1-(5-methyl-2,5-dihydro-isoxazole-3-carbonyl)-pyrrolidine-3-carboxylic acid;

1-acetyl-4-[4-({[2-(2-methoxy-phenylamino)-benzoxazol-6-yl]-acetyl}-methyl-amino)-phenyl]-pyrrolidine-3-carboxylic acid;

1-benzoyl-4-[4-({[2-(2-methoxy-phenylamino)-benzoxazol-6-yl]-acetyl}-methyl-amino)-phenyl]-pyrrolidine-3-carboxylic acid;

4-[4-({[2-(2-methoxy-phenylamino)-benzoxazol-6-yl]-acetyl}-methyl-amino)-phenyl]1-(thiophene-2-carbonyl)-pyrrolidine-3-carboxylic acid;

4-[4-({[2-(2-methoxy-phenylamino)-benzoxazol-6-yl]-acetyl}-methyl-amino)-phenyl]-1-(pyridine-4-carbonyl)-pyrrolidine-3-carboxylic acid;

4-[4-({[2-(2-methoxy-phenylamino)-benzoxazol-6-yl]-acetyl}-methyl-amino)-phenyl]-1-(morpholin-4-yl-acetyl)-pyrolidine-3-carboxylic acid;

4-[4-({[2-(2-methoxy-phenylamino)-benzoxazol-6-yl]-acetyl}-methyl-amino)-phenyl]-1-(5-methyl-2,5-dihydro-isoxazole-3-carbonyl)-pyrrolidine-3-carboxylic acid;

1-acetyl-4-(4-{2-[2-(2-ethyl-phenylamino)-benzoxazol-6-yl]-acetylamino}-phenyl)-pyrrolidine-3-carboxylic acid;

1-benzoyl-4-(4-{2-[2-(2-ethyl-phenylamino)-benzoxazol-6-yl]-acetylamino}-phenyl)-pyrrolidine-3-carboxylic acid;

4-(4-{2-[2-(2-ethyl-phenylamino)-benzoxazol-6-yl]-acetylamino}-phenyl)-1-(thiophene-2-carbonyl)-pyrrolidine-3-carboxylic acid;

4-(4-{2-[2-(2-ethyl-phenylamino)-benzoxazol-6-yl]-acetylamino}-phenyl)-1-(pyridine-4-carbonyl)-pyrrolidine-3-carboxylic acid;

4-(4-{2-[2-(2-ethyl-phenylamino)-benzoxazol-6-yl]-acetylamino}-phenyl)-1-(morpholin-4-yl-acetyl)-pyrrolidine-3-carboxylic acid;

4-(4-{2-[2-(2-ethyl-phenylamino)-benzoxazol-6-yl]-acetylamino}-phenyl)-1-(5-methyl-2,5-dihydro-isoxazole-3-carbonyl)-pyrrolidine-3-carboxylic acid;

1-acetyl-4-[4-({[2-(2-ethyl-phenylamino)-benzoxazol-6-yl]-acetyl}-methyl-amino)-phenyl]-pyrrolidine-3-carboxylic acid;

1-benzoyl-4-[4-({[2-(2-ethyl-phenylamino)-benzoxazol-6-yl]-acetyl}-methyl-amino)-phenyl]-pyrrolidine-3-carboxylic acid;

4-[4-({[2-(2-ethyl-phenylamino)-benzoxazol-6-yl]-acetyl}-methyl-amino)-phenyl]-1-(thiophene-2-carbonyl)-pyrrolidine-3-carboxylic acid;

4-[4-({[2-(2-ethyl-phenylamino)-benzoxazol-6-yl]-acetyl}-methyl-amino)-phenyl]-1-(pyridine-4-carbonyl)-pyrrolidine-3-carboxylic acid;

4-[4-({[2-(2-ethyl-phenylamino)-benzoxazol-6-yl]-acetyl}-methyl-amino)-phenyl]-1-(morpholin-4-yl-acetyl)-pyrrolidine-3-carboxylic acid;

4-[4-({[2-(2-ethyl-phenylamino)-benzoxazol-6-yl]-acetyl}-methyl-amino)-phenyl]-1-(5-methyl-2,5-dihydro-isoxazole-3-carbonyl)-pyrrolidine-3-carboxylic acid;

1-acetyl-4-(4-{2-[2-(2-chloro-phenylaminno)-benzoxazol-6-yl]-acetylamino}-phenyl)-pyrrolidine-3-carboxylic acid;

1-benzoyl-4-(4-{2-[2-(2-chloro-phenylamino)-benzoxazol-6-yl]-acetylamino}-phenyl)-pyrrolidine-3-carboxylic acid;

4-(4-{2-[2-(2-chloro-phenylamino)-benzoxazol-6-yl]-acetylamino}-phenyl)-1-(thiophene-2-carbonyl)-pyrrolidine-3-carboxylic acid;

4-(4-{2-[2-(2-chloro-phenylamino)-benzoxazol-6-yl]-acetylamino}-phenyl)-1-(pyridine-4-carbonyl)-pyrrolidine-3-carboxylic acid;

4-(4-{2-[2-(2-chloro-phenylamino)-benzoxazol-6-yl]-acetylamino}-phenyl)-1-(morpholin-4-yl-acetyl)-pyrrolidine-3-carboxylic acid;

4-(4-{2-[2-(2-chloro-phenylamino)-benzoxazol-6-yl]-acetylamino}-phenyl)-1-(5-methyl-2,5-dihydro-isoxazole-3-carbonyl)-pyrrolidine-3-carboxylic acid;

1-acetyl-4-[4-({[2-(2-chloro-phenylamino)-benzoxazol-6-yl]-acetyl}-methyl-amino)-phenyl]-pyrrolidine-3-carboxylic acid;

1-benzoyl-4-[4-({[2-(2-chloro-phenylamino)-benzoxazol-6-yl]-acetyl}-methyl-amino)-phenyl]-pyrrolidine-3-carboxylic acid;

4-[4-({[2-(2-chloro-phenylamino)-benzoxazol-6-yl]-acetyl}-methyl-amino)-phenyl]-1-(thiophene-2-carbonyl)-pyrrolidine-3-carboxylic acid;

4-[4-({[2-(2-chloro-phenylamino)-benzoxazol-6-yl]-acetyl}-methyl-amino)-phenyl]-1-(pyridine-4-carbonyl)-pyrrolidine-3-carboxylic acid;

4-[4-({[2-(2-chloro-phenylamino)-benzoxazol-6-yl]-acetyl}-methyl-amino)-phenyl]-1-(morpholin-4-yl-acetyl)-pyrrolidine-3-carboxylic acid;

4-[4-({[2-(2-chloro-phenylamino)-benzoxazol-6-yl]-acetyl}-methyl-amino)-phenyl]-1-(5-methyl-2,5-dihydro-isoxazole-3-carbonyl)-pyrrolidine-3-carboxylic acid;

1-acetyl-4-(4-{2-[2-(2,6-dimethyl-phenylamino)-benzoxazol-6-yl]-acetylamino}-phenyl)-pyrrolidine-3-carboxylic acid;

1-benzoyl-4-(4-{2-[2-(2,6-dimethyl-phenylamino)-benzoxazol-6-yl]-acetylamino}-phenyl)-pyrrolidine-3-carboxylic acid;

4-(4-{2-[2-(2,6-dimethyl-phenylamino)-benzoxazol-6-yl]-acetylamino}-phenyl)-1-(thiophene-2-carbonyl)-pyrrolidine-3-carboxylic acid;

4-(4-{2-[2-(2,6-dimethyl-phenylamino)-benzoxazol-6-yl]-acetylamino}-phenyl)-1-(pyridine-4-carbonyl)-pyrrolidine-3-carboxylic acid;

4-(4-{2-[2-(2,6-dimethyl-phenylamino)-benzoxazol-6-yl]-acetylamino}-phenyl)-1-(morpholin-4-yl-acetyl)-pyrrolidine-3-carboxylic acid;

4-(4-{2-[2-(2,6-dimethyl-phenylamino)-benzoxazol-6-yl]-acetylamino}-phenyl)-1-(5-methyl-2,5-dihydro-isoxazole-3-carbonyl)-pyrrolidine-3-carboxylic acid;

1-acetyl-4-[4-({[2-(2,6-dimethyl-phenylamino)-benzoxazol-6-yl]-acetyl}-methyl-amino)-phenyl]-pyrrolidine-3-carboxylic acid;

1-benzoyl-4-[4-({[2-(2,6-dimethyl-phenylamino)-benzoxazol-6-yl]-acetyl}-methyl-amino)-phenyl]-pyrrolidine-3-carboxylic acid;

4-[4-({[2-(2,6-dimethyl-phenylamino)-benzoxazol-6-yl]-acetyl}-methyl-amino)-phenyl]-1-(thiophene-2-carbonyl)-pyrrolidine-3-carboxylic acid;

4-[4-({[2-(2,6-dimethyl-phenylamino)-benzoxazol-6-yl]-acetyl}-methyl-amino)-phenyl]-1-(pyridine-4-carbonyl)-pyrrolidine-3-carboxylic acid;

4-[4-({[2-(2,6-dimethyl-phenylamino)-benzoxazol-6-yl]-acetyl}-methyl-ammo)-phenyl]-1-(morpholin-4-yl-acetyl)-pyrrolidine-3-carboxylic acid;

4-[4-({[2-(2,6-dimethyl-phenylamino)-benzoxazol-6-yl]-acetyl}-methyl-amino)-phenyl]-1-(5-methyl-2,5-dihydro-isoxazole-3-carbonyl)-pyirolidine-3-carboxylic acid;

1-acetyl-4-(4-{2-[2-(3-cyano-phenylamino)-benzoxazol-6-yl]-acetylamino}-phenyl)-pyrrolidine-3-carboxylic acid;

1-benzoyl-4-(4-{2-[2-(3-cyano-phenylamino)-benzoxazol-6-yl]-acetylamino}-phenyl)-pyrrolidine-3-carboxylic acid;

4-(4-{2-[2-(3-cyano-phenylamino)-benzoxazol-6-yl]-acetylamino}-phenyl)-1-(thiophene-2-carbonyl)-pyrrolidine-3-carboxylic acid;

4-(4-{2-[2-(3-cyano-phenylamino)-benzoxazol-6-yl]-acetylamino}-phenyl)-1-(pyridine-4-carbonyl)-pyrrolidine-3-carboxylic acid;

4-(4-{2-[2-(3-cyano-phenylamino)-benzoxazol-6-yl]-acetylamino}-phenyl)-1-(morpholin-4-yl-acetyl)-pyrrolidine-3-carboxylic acid;

4-(4-{2-[2-(3-cyano-phenylamino)-benzoxazol-6-yl]-acetylamino}-phenyl)-1-(5-methyl-2,5-dihydro-isoxazole-3-carbonyl)-pyrrolidine-3-carboxylic acid;

1-acetyl-4-[4-({[2-(3-cyano-phenylamino)-benzoxazol-6-yl]-acetyl}-methyl-amino)-phenyl]-pyrrolidine-3-carboxylic acid;

1-benzoyl-4-[4-({[2-(3-cyano-phenylamino)-benzoxazol-6-yl]-acetyl}-methyl-amino)-phenyl]-pyrrolidine-3-carboxylic acid;

4-[4-({[2-(3-cyano-phenylamino)-benzoxazol-6-yl]-acetyl}-methyl-amino)-phenyl]-1-(thiophene-2-carbonyl)-pyrrolidine-3-carboxylic acid;

4-[4-({[2-(3-cyano-phenylamino)-benzoxazol-6-yl]-acetyl}-methyl-amino)-phenyl]-1-(pyridine-4-carbonyl)-pyrrolidine-3-carboxylic acid;

4-[4-({[2-(3-cyano-phenylamino)-benzoxazol-6-yl]-acetyl}-methyl-amino)-phenyl]-1-(morpholin-4-yl-acetyl)-pyrrolidine-3-carboxylic acid;

4-[4-({[2-(3-cyano-phenylamino)-benzoxazol-6-yl]-acetyl}-methyl-amino)-phenyl]-1-(5-methyl-2,5-dihydro-isoxazole-3-carbonyl)-pyrrolidine-3-carboxylic acid;

1-acetyl-4-(4-{2-[2-(3-methoxy-phenylamino)-benzoxazol-6-yl]-acetylamino}-phenyl)-pyrrolidine-3-carboxylic acid;

1-benzoyl-4-(4-{2-[2-(3-methoxy-phenylamino)-benzoxazol-6-yl]-acetylamino}-phenyl)-pyrrolidine-3-carboxylic acid;

4-(4-{2-[2-(3-methoxy-phenylamino)-benzoxazol-6-yl]-acetylamino}-phenyl)-1-(thiophene-2-carbonyl)-pyrrolidine-3-carboxylic acid;

4-(4-{2-[2-(3-methoxy-phenylamino)-benzoxazol-6-yl]-acetylamino}-phenyl)-1-(pyridine-4-carbonyl)-pyrrolidine-3-carboxylic acid;

4-(4-{2-[2-(3-methoxy-phenylamino)-benzoxazol-6-yl]-acetylamino}-phenyl)-1-(morpholin-4-yl-acetyl)-pyrrolidine-3-carboxylic acid;

4-(4-{2-[2-(3-methoxy-phenylamino)-benzoxazol-6-yl]-acetylamino}-phenyl)-1-(5-methyl-2,5-dihydro-isoxazole-3-carbonyl)-pyrrolidine-3-carboxylic acid;

1-acetyl-4-[4-({[2-(3-methoxy-phenylamino)-benzoxazol-6-yl]-acetyl}-methyl-amino)-phenyl]-pyrrolidine-3-carboxylic acid;

1-benzoyl-4-[4-({[2-(3-methoxy-phenylamino)-benzoxazol-6-yl]-acetyl}-methyl-amino)-phenyl]-pyrrolidine-3-carboxylic acid;

4-[4-({[2-(3-methoxy-phenylamino)-benzoxazol-6-yl]-acetyl}-methyl-amino)-phenyl]-1-(thiophene-2-carbonyl)-pyrrolidine-3-carboxylic acid;

4-[4-({[2-(3-methoxy-phenylamino)-benzoxazol-6-yl]-acetyl}-methyl-amino)-phenyl]-1-(pyridine-4-carbonyl)-pyrrolidine-3-carboxylic acid;

4-[4-({[2-(3-methoxy-phenylamino)-benzoxazol-6-yl]-acetyl}-methyl-amino)-phenyl]-1-(morpholin-4-yl-acetyl)-pyrrolidine-3-carboxylic acid;

4-[4-({[2-(3-methoxy-phenylamino)-benzoxazol-6-yl]-acetyl}-methyl-amino)-phenyl]-1-(5-methyl-2,5-dihydro-isoxazole-3-carbonyl)-pyrrolidine-3-carboxylic acid;

1-acetyl-4-{4-[2-(2-phenylamino-benzoxazol-6-yl)-acetylamino]-phenyl}-pyrrolidine-3-carboxylic acid;

1-benzoyl-4-{4-[2-(2-phenylamino-benzoxazol-6-yl)-acetylamino]-phenyl}-pyrrolidine-3-carboxylic acid;

4-{4-[2-(2-phenylamino-benzoxazol-6-yl)-acetylamino]-phenyl}-1-(thiophene-2-carbonyl)-pyrrolidine-3-carboxylic acid;

4-{4-[2-(2-phenylamino-benzoxazol-6-yl)-acetylamino]-phenyl}-1-(pyridine-4-carbonyl)-pyrrolidine-3-carboxylic acid;

1-(morpholin-4-yl-acetyl)4-{4-[2-(2-phenylamino-benzoxazol-6-yl)-acetylamino]-phenyl}-pyrrolidine-3-carboxylic acid;

1-(5-methyl-2,5-dihydro-isoxazole-3-carbonyl)4-{4-[2-(2-phenylamino-benzoxazol-6-yl)-acetylamino]-phenyl}-pyrrolidine-3-carboxylic acid;

1-acetyl-4-(4-{methyl-[(2-phenylamino-benzoxazol-6-yl)-acetyl]-amino}-phenyl)-pyrrolidine-3-carboxylic acid;

1-benzoyl-4-(4-{methyl-[(2-phenylamino-benzoxazol-6-yl)-acetyl]-amino}-phenyl)-pyrrolidine-3-carboxylic acid;

4-(4-{methyl-[(2-phenylamino-benzoxazol-6-yl)-acetyl]-amino}-phenyl)-1-(thiophene-2-carbonyl)-pyrrolidine-3-carboxylic acid;

4(4{methyl-[(2-phenylamino-benzoxazol-6-yl)-acetyl]-amino}-phenyl)-1-(pyridine-4-carbonyl)-pyrrolidine-3-carboxylic acid;

4-(4-{methyl-[(2-phenylamino-benzoxazol-6-yl)-acetyl]-amino}-phenyl)-1-(morpholin-4-yl-acetyl)-pyrrolidine-3-carboxylic acid;

1-(5-methyl-2,5-dihydro-isoxazole-3-carbonyl)4-(4-{methyl-[(2-phenylamino-benzoxazol-6-yl)-acetyl]-amino}-phenyl)-pyrrolidine-3-carboxylic acid;

1-acetyl-4-(4-{2-[2-(pyridin-3-ylamino)-benzoxazol-6-yl]-acetylamino}-phenyl)-pyrrolidine-3-carboxylic acid;

1-benzoyl-4-(4-{2-[2-(pyridin-3-ylamino)-benzoxazol-6-yl]-acetylamino}-phenyl)-pyrrolidine-3-carboxylic acid;

4-(4-{2-[2-(pyridin-3-ylamino)-benzoxazol-6-yl]-acetylamino}-phenyl)-1-(thiophene-2-carbonyl)-pyrrolidine-3-carboxylic acid;

1-(pyridine-4-carbonyl)4-(4-{2-[2-(pyridin-3-ylamino)-benzoxazol-6-yl]-acetylamino}-phenyl)-pyrrolidine-3-carboxylic acid;

1-(morpholin-4-yl-acetyl)4-(4-{2-[2-(pyridin-3-ylamino)-benzoxazol-6-yl]-acetylamino}-phenyl)-pyrrolidine-3-carboxylic acid;

1-(5-methyl-2,5-dihydro-isoxazole-3-carbonyl)-4-(4-{2-[2-(pyridin-3-ylamino)-benzoxazol-6-yl]-acetylamino}-phenyl)-pyrrolidine-3-carboxylic acid;

1-acetyl-4-[4-(methyl-{[2-(pyridin-3-ylamino)-benzoxazol-6-yl]-acetyl}-amino)-phenyl]-pyrrolidine-3-carboxylic acid;

1-benzoyl-4-[4-(methyl-{[2-(pyridin-3-ylamino)-benzoxazol-6-yl]-acetyl}-amino)-phenyl]-pyrrolidine-3-carboxylic acid;

4-[4-(methyl-{[2-(pyridin-3-ylamino)-benzoxazol-6-yl]-acetyl}-amino)-phenyl]-1-(thiophene-2-carbonyl)-pyrrolidine-3-carboxylic acid;

4-[4-(methyl-{[2-(pyridin-3-ylamino)-benzoxazol-6-yl]-acetyl}-amino)-phenyl]-1-(pyridine-4-carbonyl)-pyrrolidine-3-carboxylic acid;

4-[4-(methyl-{[2-(pyridin-3-ylamino)-benzoxazol-6-yl]-acetyl}-amino)-phenyl]-1-(morpholin-4-yl-acetyl)-pyrrolidine-3-carboxylic acid;

1-(5-methyl-2,5-dihydro-isoxazole-3-carbonyl)-4-[4-(methyl-{[2-(pyridin-3-ylamino)-benzoxazol-6-yl]-acetyl}-amino)-phenyl]-pyrrolidine-3-carboxylic acid;

1-acetyl-4-(4-{2-[2-(2-chloro-6-methyl-phenylamino)-benzoxazol-6-yl]-acetylamino}-phenyl)-pyrrolidine-3-carboxylic acid;

1-benzoyl-4-(4-{2-[2-(2-chloro-6-methyl-phenylamino)-benzoxazol-6-yl]-acetylamino}-phenyl)-pyrrolidine-3-carboxylic acid;

4-(4-{2-[2-(2-chloro-6-methyl-phenylamino)-benzoxazol-6-yl]-acetylamino}-phenyl)-1-(thiophene-2-carbonyl)-pyrrolidine-3-carboxylic acid;

4-(4-{2-[2-(2-chloro-6-methyl-phenylamino)-benzoxazol-6-yl]-acetylamino}-phenyl)-1-(pyridine-4-carbonyl)-pyrrolidine-3-carboxylic acid;

4-(4-{2-[2-(2-chloro-6-methyl-phenylamino)-benzoxazol-6-yl]-acetylamino}-phenyl)-1-(morpholin-4-yl-acetyl)-pyrrolidine-3-carboxylic acid;

4-(4-{2-[2-(2-chloro-6-methyl-phenylamino)-benzoxazol-6-yl]-acetylamino}-phenyl)-1-(5-methyl-2,5-dihydro-isoxazole-3-carbonyl)-pyrrolidine-3-carboxylic acid;

1-acetyl-4-[4-({[2-(2-chloro-6-methyl-phenylamino)-benzoxazol-6-yl]-acetyl}-methyl-amino)-phenyl]-pyrrolidine-3-carboxylic acid;

1-benzoyl-4-[4-({[2-(2-chloro-6-methyl-phenylamino)-benzoxazol-6-yl]-acetyl}-methyl-amino)-phenyl]-pyrrolidine-3-carboxylic acid;

4-[4-({[2-(2-chloro-6-methyl-phenylamino)-benzoxazol-6-yl]-acetyl}-methyl-amino)-phenyl]-1-(thiophene-2-carbonyl)-pyrrolidine-3-carboxylic acid;

4-[4-({[2-(2-chloro-6-methyl-phenylamino)-benzoxazol-6-yl]-acetyl}-methyl-amino)-phenyl]-1-(pyridine-4-carbonyl)-pyrrolidine-3-carboxylic acid;

4-[4-({[2-(2-chloro-6-methyl-phenylamino)-benzoxazol-6-yl]-acetyl}-methyl-amino)-phenyl]-1-(morpholin-4-yl-acetyl)-pyrrolidine-3-carboxylic acid;

4-[4-({[2-(2-chloro-6-methyl-phenylamino)-benzoxazol-6-yl]-acetyl}-methyl-amino)-phenyl]-1-(5-methyl-2,5-dihydro-isoxazole-3-carbonyl)-pyrrolidine-3-carboxylic acid;

and their prodrugs, and pharmaceutically acceptable salts and solvates (e.g. hydrates) of such compounds and their prodrugs.

Preferred compounds of the invention are:

1-benzoyl-4-(4-{2-[3-methoxy-4-(3-o-tolyl-ureido)-phenyl]-acetylamino}-phenyl)-pyrrolidine-3-carboxylic acid;

1-acetyl-4-(4-{2-[3-methoxy-4-(3-o-tolyl-ureido)-phenyl]-acetylamino}-phenyl)-pyrrolidine-3-carboxylic acid;

1-(3-carboxy-propionyl)4-(4-{2-[3-methoxy-4-(3-o-tolyl-ureido)-phenyl]-acetylamino}-phenyl)-pyrrolidine-3-carboxylic acid;

and their prodrugs, and pharmaceutically acceptable salts and solvates (e.g. hydrates) of such compounds and their prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 ($\alpha 4\beta 1$) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of $\alpha 4\beta 1$ mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 ($\alpha 4\beta 1$), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 ($\alpha 4\beta 1$), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler. Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to 15;t obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I) wherein $R^1$, $L^1$, $Ar^1$, $A^1$, $A^2$ and $A^3$ are as hereinbefore defined, and Y is carboxy may be prepared by hydrolysis of esters of formula (I) wherein $R^1$, $L^1$, $Ar^1$, $A^1$, $A^2$ and $A^3$ are as hereinbefore defined and where the Y is a —$CO_2R^{20}$ group (in which $R^{20}$ is alkyl, alkenyl or arylalkyl). The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) wherein $R^1$, $L^1$, $Ar^1$, $A^1$, $A^2$ and $A^3$ are as hereinbefore defined, and Y is carboxy may be prepared by acid catalysed removal of the tert-butyl group of tert-butyl esters of formula (I) wherein $R^1$, $L^1$, $Ar^1$, $A^1$, $A^2$ and $A^3$ are as hereinbefore defined and Y is a —$CO_2R^{20}$ group (in which $R^{20}$ is tert-butyl), using standard reaction conditions, for example reaction with trifluoroacetic acid at a temperature at about room temperature.

As another example of compounds of formula (I) wherein $R^1$, $L^1$, $Ar^1$, $A^1$, $A^2$ and $A^3$ are as hereinbefore defined and Y is carboxy may be prepared by hydrogenation of compounds of formula (I) wherein $R^1$, $L^1$, $Ar^1$, $A^1$, $A^2$ and $A^3$ are as hereinbefore defined and Y is a —$CO_2R^{20}$ group (in which $R^{20}$ is benzyl). The reaction may be carried out in the presence of ammonium formate and a suitable metal catalyst, e.g. palladium, supported on an inert carrier such as carbon, preferably in a solvent such as methanol or ethanol and at a temperature about reflux temperature. The reaction may alternatively be carried out in the presence of a suitable metal catalyst, e.g. platinum or palladium optionally supported on an inert carrier such as carbon, preferably in a solvent such as methanol or ethanol.

In a process A compounds of formula (I), containing an amide bond may be prepared by coupling of an acid (or an acid halide) with an amine to give an amide bond using standard peptide coupling procedures as described hereinafter.

As an example of process A, compounds of formula (I) wherein $R^1$, $Ar^1$, $A^1$, $A^2$ and $A^3$ are as hereinbefore defined, $L^1$ is —$R^{12}$—$R^{13}$— (in which $R^{12}$ is hereinbefore defined and $R^{13}$ is —C(=O)—$NR^{11}$—) and Y is a —$CO_2R^{20}$ group (in which $R^{20}$ is hereinbefore defined) may be prepared by reaction of compounds of formula (II):

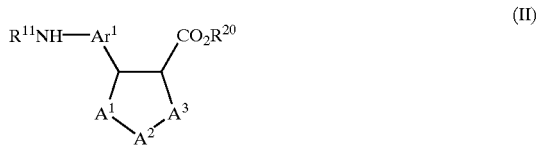

(II)

wherein $R^{11}$, $R^{20}$, $Ar^1$, $A^1$, $A^2$ and $A^3$ are as hereinbefore defined with compounds of formula (III):

(III)

wherein $R^1$ and $R^{12}$ are as hereinbefore defined, and $X^4$ is a hydroxy group or a halogen, preferably chlorine, atom. When $X^4$ is a hydroxy group the reaction may be carried out using standard peptide coupling procedures for example coupling in the presence of benzotriazol-1lyloxytris (dimethylamino)phosphonium hexafluorophosphate and triethylamine (or diisopropylethylamine) and dimethylaminopyridine in tetrahydrofuran (or dimethylformamide), at room temperature. When $X^4$ is a halogen atom the acylation reaction may be carried out with the aid of a base, such pyridine, preferably in a solvent such as tetrahydrofuran and at a temperature at about room temperature.

As another example of process A, compounds of formula (I) wherein $R^1$, $L^1$, $Ar^1$ are as hereinbefore defined, Y is carboxy and one of $A^1$, $A^2$ and $A^3$ is $NR^2$ (in which $R^2$ is —C(=O)—$R^8$) whilst the others represent $C(R^3)(R^4)$ may be prepared by reaction of compounds of formula (IV):

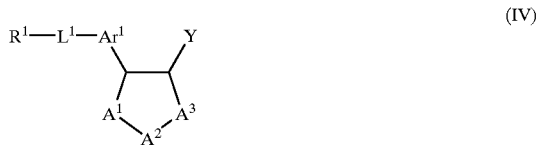

(IV)

wherein $R^1$, $L^1$ and $Ar^1$ are as hereinbefore defined, Y is carboxy and one of $A^1$, $A^2$ and $A^3$ is NH and the others represent $C(R^3)(R^4)$ with compounds of formula (V):

(V)

wherein $R^8$ is as defined hereinbefore and $X^5$ is a halogen, preferably chlorine, atom. The acylation reaction may conveniently be carried out using standard reaction conditions for example those described hereinbefore.

Esters of formula (I) wherein $R^1$, $L^1$, $Ar^1$ are as hereinbefore defined, Y is a —$CO_2R^{20}$ group (in which $R^{20}$ is as hereinbefore defined) and one of $A^1$, $A^2$ and $A^3$ is $NR^2$ (in which $R^2$ is —C(=O)—$R^8$) whilst the others represent $C(R^3)(R^4)$ may be similarly prepared by reaction of compounds of formula (IV) wherein $R^1$, $L^1$ and $Ar^1$ are as hereinbefore defined, Y is a —CO$_2$R$^{20}$ group (in which R$^{20}$ is as hereinbefore defined) and one of A$^1$, A$^2$ and A$^3$ is NH whilst the others represent C(R$^3$)(R$^4$) with compounds of formula (V) wherein R$^8$ is as defined hereinbefore and X$^5$ is a hydroxy group or a halogen, preferably chlorine, atom, using standard reaction conditions for example those described hereinbefore.

According to a further feature of the present invention, compounds of the invention may be prepared by interconversion of other compounds of the invention.

For example compounds of formula (I) wherein R$^1$, L$^1$, Ar$^1$, A$^1$, A$^2$ and A$^3$ are as hereinbefore defined, and Y is —C(=O)—NHOH, may be prepared by reaction of compounds of formula (I) wherein R$^1$, L$^1$, Ar$^1$, A$^1$, A$^2$ and A$^3$ are as hereinbefore defined, and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl) hydroxylamine, O-(t-butyldimethylsilyl)-hydroxylamine, or O-(tetrahydropyranyl)hydroxylamine followed by treatment with acid.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates. As an example compounds of formula (I) wherein Y is carboxy may coupled with camphor sultame, followed by separation of the diastereoisomers and then regeneration of the individual isomers of compounds of formula (I) by treatment with aqueous sodium hydroxide solution, in methanol, at a temperature at about room temperature.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Compounds of formula (II) wherein R$^{20}$, Ar$^1$, A$^1$, A$^2$ and A$^3$ are as hereinbefore defined and R$^{11}$ is hydrogen, may be prepared by reduction of the corresponding nitro compounds of formula (1):

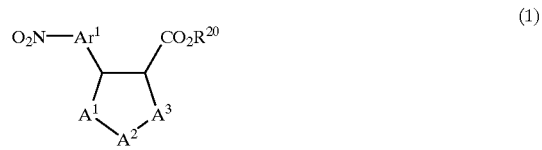

(1)

wherein R$^{20}$, Ar$^1$, A$^1$, A$^2$ and A$^3$ are as hereinbefore defined. The reduction may conveniently be carried out using standard methods for the reduction of aromatic nitro compounds to the corresponding aromatic amines, for example (i) treatment with tin chloride in an inert solvent, such as ethyl acetate or dimethylformamide, at a temperature at about 70° C., (ii) treatment with tin in the presence of hydrochloric acid in ethanol at a temperature at about reflux temperature or (iii) hydrogenation in the presence of palladium on carbon.

Compounds of formula (1) wherein R$^{20}$ and Ar$^1$ are as hereinbefore defined, one A$^1$, A$^2$ and A$^3$ represents NR$^2$ [in which R[2] is —C(=O)—R[8]] and the others represent C(R[3])(R[4]), may be prepared by reaction compounds of formula (1) wherein R[20] and Ar[1] are as hereinbefore defined, one A[1], A[2] and A[3] represents NH and the others represent C(R[3])(R[4]), with compounds of formula (2):

R[8]—C(=O)—X[6]     (2)

wherein R[8] is as hereinbefore defined and X[6] is a hydroxy group or a halogen, preferably chlorine, atom. The reaction may be carried out by standard peptide coupling or acylation procedures for example those described hereinbefore.

Compounds of formula (1) wherein R[20] and Ar[1] are as hereinbefore defined, one A[1], A[2] and A[3] represents NR[2] [in which R[2] is —C(=O)—OR[8a]] and the others represent C(R[3])(R[4]), may be prepared by reaction compounds of formula (1) wherein R[20] and Ar[1] are as hereinbefore defined, one A[1], A[2] and A[3] represents NH and the others represent C(R[3])(R[4]), with compounds of formula (3):

R[8a]O—C(=O)—Cl     (3)

wherein R[8a] is as hereinbefore defined. The reaction may be carried out by standard acylation procedures for example those described hereinbefore.

Compounds of formula (1) wherein R[20] and Ar[1] are as hereinbefore defined, one A[1], A[2] and A[3] represents NR[2] [in which R[2] is R[8b]] and the others represent C(R[3])(R[4]), may be prepared by reaction compounds of formula (1) wherein R[20] and Ar[1] are as hereinbefore defined, one A[1], A[2] and A[3] represents NH and the others represent C(R[3])(R[4]), with compounds of formula (4):

R[8b]—X[7]     (4)

wherein R[8b] is as hereinbefore defined and X[7] is a hydroxy group or a halogen, preferably chlorine, atom The reaction may be carried out by standard alkylation procedures for example those described hereinbefore.

Compounds of formula (1) wherein R[20] and Ar[1] are as hereinbefore defined, one A[1], A[2] and A[3] represents NH and the others represent C(R[3])(R[4]), may be prepared by reaction of compounds of formula (1) wherein R[20] and Ar[1] are as hereinbefore defined, one A[1], A[2] and A[3] represents N—C(=O)—O—CH=CH[2] and the others represent C(R[3])(R[4]), with a mineral acid, such as hydrochloric acid, in an inert solvent, such as dioxane and at a temperature at about room temperature.

Compounds of formula (1) wherein R[20] and Ar[1] are as hereinbefore defined, one A[1], A[2] and A[3] represents N—C(=O)—O—CH=CH[2] and the others represent C(R[3])(R[4]), may be prepared by reaction of compounds of formula (1) wherein R[20] and Ar[1] are as hereinbefore defined, one A[1], A[2] and A[3] represents N—CH[2]Ph and the others represent C(R[3])(R[4]), with vinyl chloroformate at reflux temperature.

Compounds of formula (1) wherein R[20] and Ar[1] are as hereinbefore defined, A[1] and A[3] represent CH[2], A[2] represents N—CH[2]Ph, may be prepared by reaction of compounds of formula (5):

O[2]N—Ar[1]—CH=CH—CO[2]R[20]     (5)

wherein R[20] and Ar[1] are as hereinbefore defined, with N-(butoxymethyl)-N-(trimethylsilylmethyl)benzylamine in the presence of trifluoroacetic acid and at a temperature at about room temperature.

Compounds of formula (1) wherein R[20] and Ar[1] are as hereinbefore defined, A[2] and A[3] represent CH[2] and A[1] represents N—C(=O)—R[8], may be prepared by reaction of compounds of formula (6):

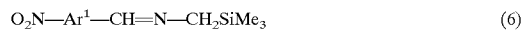
O[2]N—Ar[1]—CH=N—CH[2]SiMe[3]     (6)

wherein Ar[1] is as hereinbefore defined, with an acrylate ester of formula (7):

CH[2]=CH—CO[2]R[20]     (7)

wherein R[20] is as hereinbefore defined, and an acid chloride of formula (2) wherein R[8] and X[6] are as hereinbefore defined, in an inert solvent, such as tetrahydrofuran, and at a temperature at about reflux temperature.

Compounds of formula (6) wherein Ar[1] is as hereinbefore defined may be prepared by the application or adaptation of the methods of K. Achiwa et al, Chem. Pharm. Bull., 1983, 31, page 3939.

Compounds of formula (IV) wherein R[1], L[1] and Ar[1] are as hereinbefore defined, Y is carboxy and one of A[1], A[2] and A[3] is NH whilst the others represent C(R[3])(R[4]) may be prepared by hydrogenation of compounds of formula (I) wherein R[1], L[1] and Ar[1] are as hereinbefore defined, Y is carboxy and one of A[1], A[2] and A[3] is NCH[2]Ph whilst the others represent C(R[3])(R[4]). The hydrogenation may conveniently be carried out in the presence of palladium hydroxide in acetic acid under pressure and at a temperature at about room temperature.

Intermediates of formulae (II), (IV) and (1) are novel compounds and, as such, they and their processes described herein for their preparation constitute further features of the present invention.

Intermediates of formulae (IV) are also able to regulate the interaction of VCAM-1 and fibronectin with the integrin VLA-4.

The present invention is further Exemplified but not limited by the following illustrative Examples and Reference Examples.

1H spectra NMR at 600 MHz were recorded on DMX 600 Bruker. 1H spectra NMR at 500 MHz were recorded on DRX 500 Bruker. 1H spectra NMR at 400 MHz were recorded on DRX 400 Bruker. 1H spectra NMR at 300 MHz were recorded on AC 300 Bruker. 1H spectra NMR at 250 MHz were recorded on AC 250 Bruker. b=broad signal, bd=broad doublet, bs=broad singlet, bt=broad triplet, d=doublet, dd=double doublet, m=multiplet, s=singlet, t=triplet, 2bs=two broad singlets, 2d=two doublets, 2m =two multiplets, 2s=two singlets, Desorption Chemical Ionization Mass Spectra, MS (DCI), were recorded on a Finnigan SSQ 7000 spectrometer using ammonia as the reactant gas.

Electron Impact Mass Spectra, MS (EI), were recorded on a Finnigan SSQ 7000 spectrometer at 70eV.

Fast Atom Bombardment Mass Spectra, MS(FAB), were recorded on an Autospec micromass.

Liquid Secondary Ion Mass Spectra, MS(LSIMS), were recorded on a VG AutoSpec spectrometer using a mixture of glycerol-thioglycerol 50/50 as the matrix.

EXAMPLE 1

1-Acetyl-4-(4-{2-[3-methoxy-4-(3-o-tolyl-ureido)-phenyl]-acetylamino}-phenyl)-pyrrolidine-3-carboxylic Acid.

A solution of 1-acetyl-4-(4-{2-[3-methoxy-4-(3-o-tolyl-ureido)-phenyl]-acetylamino}-phenyl)-pyrrolidine-3-carboxylic acid ethyl ester (1.62 g, Reference Example 1) in anhydrous ethanol (60 ml) was treated dropwise with sodium hydroxide solution (48 ml, 0.1 M). After stirring for 15 hours at 23° C. the mixture was evaporated (40° C. and 2.7 kPa). The residue was diluted with distilled water (200 ml), then cooled to 5° C. and then the pH of the mixture was adjusted to 2 by dropwise addition of hydrochloric acid (1N)

resulting in the precipitation of a white solid. After stirring at 23° C. for 15 hours the mixture was filtered. The white solid was dried under reduced pressure (2.7 kPa) then triturated with ether affording the title compound (1 g) as a white solid, m.p. 242° C. $^1$H-NMR [600 MHz, (CD$_3$)$_2$SO]: δ 1.95 and 1.98 (2 s, 3H); 2.25 (s, 3H); 3.10 to 3.95 (m, 6H); 3.58 (s, 2H); 3.89 (s, 3H); 6.85 (bd, J=8 Hz, 1H); 6.95 (t, J=7.5 Hz, 1H); 7.02 (bs, 1H); 7.13 (t, J=7.5 Hz, 1H); 7.17 (d, J=7.5 Hz, 1H); 7.25 and 7.28 (2 d, J=8 Hz, 2H); 7.50 to 7.60 (m, 2H); 7.80 (d, J=7.5 Hz, 1H); 8.04 (d, J=8 Hz, 1H); 8.48 (s, 1H); 8.59 (s, 1H). MS [FAB (meta-nitrobenzylalcohol)]: 545 [M+H]$^+$.

EXAMPLE 2

1-Benzoyl-4-(4-{2-[3-methoxy-4-(3-o-tolyl-ureido)-phenyl]-acetylamino}-phenyl)-pyrrolidine-3-carboxylic Acid A stirred solution of 1-benzoyl-4-(4-{2-[3-methoxy-4-(3-o-tolyl-ureido)-phenyl]-acetylamino}-phenyl)-pyrrolidine-3-carboxylic acid ethyl ester (5 g, Reference Example 7) in ethanol (60 ml), at 23° C., was treated dropwise with sodium hydroxide solution (16 ml, 1N). After stirring for 24 hours the mixture was evaporated (40° C. and 2.7 kPa) and the residue was treated with water (300 ml). The mixture was cooled to 10° C, then treated with hydrochloric acid (25 ml, 1N) and then stood at 23° C. for 20 hours. The resulting white precipitate was filtered, then dried under reduced pressure (40° C. and 2.7 kPa) for 45 minutes and then recrystallised from aqueous ethanol (40 ml) affording the title compound (3.25 g) as a white crystalline powder, m.p. 248° C. TLC: R$_F$=45/78 (on silica eluting with a mixture of dichloromethane and methanol, 90:10). $^1$H-NMR [500 MHz, (CD$_3$)$_2$SO at 373°K.]: δ 2.29 (s, 3H); 3.26 (m, 1H); 3.50 to 3.65 (m, 2H); 3.61 (s, 2H); 3.76 (m, 1H);3.85 to 4.00 (m, 2H); 3.91 (s, 3H); 6.88 (d, J=8 Hz, 1H); 6.99 (t, J=7.5 Hz, 1H); 7.03 (bs, 1H); 7.14 (t, J=7.5 Hz, 1H); 7.18 (d, J=7.5 Hz, 1H); 7.26 (d, J=8.5 Hz, 2H); 7.45 (m, 3H); 7.55 (m, 4H); 7.70 (d, J=7.5 Hz, 1H); 8.01 (d, J=8 Hz, 1H); 8.10 (bs, 1H); 8.26 (bs, 1H); 9.64 (bs, 1H); 11.50 to 12.30 (b, 1H). MS [FAB (meta-nitrobenzylalcohol)]: 607 [M+H]$^+$.

EXAMPLE 3

1-(3-Carboxy-propionyl)-4-(4-{2-[3-methoxy-4-(3-o-tolyl-ureido)-phenyl]-acetylamino}-phenyl)-pyrrolidine-3-carboxylic Acid A stirred solution of 1-(3-ethoxycarbonyl-propionyl)4-(4-{2-[3-methoxy-4-(3-o-tolyl-ureido)-phenyl]-acetylamino}-phenyl)-pyrrolidine-3-carboxylic acid ethyl ester (0.3 g, Reference Example 10) in ethanol (3 ml) was treated dropwise with aqueous sodium hydroxide solution (1.8 ml and then 0.9 ml after 20 hours, 1N). After stirring at 20° C. for a further 2 hours the mixture was evaporated (40° C. and 2.7 kPa). The residue was treated with water (50 ml), then cooled to 5° C. and the pH of the mixture adjusted to 2 by dropwise addition of hydrochloric acid (10 ml, 1 N). The aqueous solution was triturated with ethyl acetate (50 ml), affording the title compound (130 mg) as a white solid, m.p. 184° C. TLC: R$_F$=0.5 (on silica eluting with a mixture of dichloromethane and methanol, 50:50).

$^1$H-NMR [400 MHz, (CD$_3$)$_2$SO at 413° K.]: δ 2.31 (s, 3H); 2.50 to 2.60 (m, 4H); 3.20 (m, 1H); 3.46 (m, 1H); 3.55 to 3.70 (m, 2H); 3.63 (s, 2H); 3.85 to 4.00 (m, 2H); 3.90 (s, 3H); 6.90 (bd, J=8 Hz, 1H); 7.01 (t, J=7.5 Hz, 1H); 7.04 (bs, 1H); 7.15 (t, J=7.5 Hz, 1H); 7.20 (d, J=7.5 Hz, 1H); 7.26 (d, J=8.5 Hz, 2H); 7.54 (d, J=8.5 Hz, 2H); 7.66 (d, J=7.5 Hz, 1H); 7.98 (d, J=8 Hz, 1H); 8.01 (bs, 1H); 8.10 (bs, 1H); 9.36 (bs, 1H). MS: [FAB (glycerol +thioglycerol)]: 603 [M+H]$^+$.

EXAMPLE 4

1-Benzoyl-2-(4-{2-[3-methoxy-4-(3-o-tolyl-ureido)-phenyl]-acetylamino}-phenyl)-pyrrolidine-3-carboxylic Acid A stirred solution of 1-benzoyl-2-(4-{2-[3-methoxy-4-(3-o-tolyl-ureido)-phenyl]-acetylamino}-phenyl)-pyrrolidine-3-carboxylic acid ethyl ester (0.33 g, Reference Example 13) in a mixture of ethanol (4 ml) and acetonitrile (40 ml), at 20° C., was treated dropwise with aqueous sodium hydroxide solution (0. 15 ml, 10 N). After stirring for 6 days the mixture was filtered and the insoluble light brown solid was triturated twice with acetonitrile (5 ml), then twice with dichloromethane (2.5 ml) and then dried. The solid was dissolved in water (30 ml) and filtered. The filtrate was cooled to 5° C. and the pH of the mixture adjusted to 2 by dropwise addition of hydrochloric acid (1.2 ml, 1N). The resulting white precipitate was filtered then washed three times with water (5 ml), then twice with diisopropyl ether (10 ml) and then dried under reduced pressure (40° C. and 2.7 kPa) to afford the title compound (0.134 g) as an off-white powder, m.p. 155° C. (with decomposition). $^1$H-NMR [500 MHz, (CD$_3$)$_2$SO at 383° K.]: δ 2.15 (m, 2H); 2.27 (s, 3H); 2.96 (m, 1H); 3.59 (s, 2H); 3.75 (m, 2H); 3.89 (s, 3H); 5.32 (m, 1H); 6.87 (bd, J=8 Hz, 1H); 6.98 (t, J=7.5 Hz, 1H); 7.02 (d, J=1.5 Hz, 1H); 7.10 to 7.25 (m, 4H); 7.30 to 7.45 (m, 5H); 7.52 (d, J=8.5 Hz, 2H); 7.67 (d, J=8 Hz, 1H); 7.99 (d, J=8 Hz, 1H); 8.15 (bs, 1H); 8.21 (bs, 1H); 9.55 (bs, 1H). MS(ES): 629 [M+Na]$^+$.

EXAMPLE 5

1-Benzyl-4-(4-{2-[3-methoxy-4-(3-o-tolyl-ureido)-phenyl]-acetylamino}-phenyl)-pyrrolidine-3-carboxylic Acid A stirred solution of 1-benzyl-4-(4-{2-[3-methoxy-4-(3-o-tolyl-ureido)-phenyl]-acetylamino}-phenyl)-pyrrolidine-3-carboxylic acid ethyl ester (2.95 g, Reference Example 16) in a mixture of acetonitrile (150 mL) and ethanol (125 mL), at 50° C., was treated slowly with aqueous sodium hydroxide solution (0.46 mL, 30%). After stirring for 8 hours at room temperature and then gentle stirring for a week, the mixture was filtered. The solid was washed with dichloromethane (30 mL), then dried under reduced pressure (2.7 kPa) and then treated with water (200 mL). The mixture was acidified by addition of hydrochloric acid (3.5 mL, 1 M), then allowed to stand at room temperature for 15 hours, then treated with ethyl acetate (400 mL) and then filtered to give the title compound (1.16 g) as a white powder, m.p. 255° C. $^1$H-NMR [400 MHz, (CD$_3$)$_2$SO]: δ 2.27 (s, 3H); 2.45 to 2.60 (m, 1H); 2.80 to 3.00 (m, 4H); 3.49 (m, 1H); 3.57 (s, 2H); 3.58 and 3.68 (2 d, J=14 Hz, 2H); 3.90 (s, 3H); 6.85 (bd, J=8 Hz, 1H); 6.95 (bt, J=7 Hz, 1H); 7.02 (bs, 1H); 7.05 to 7.20 (m, 2H); 7.20 to 7.30 (m, 3H); 7.30 to 7.40 (m, 4H); 7.52 (bd, J=8 Hz, 2H); 7.82 (bd, J=8 Hz, 1H); 8.04 (d, J=8 Hz, 1H); 8.48 (bs, 1H); 8.59 (bs, 1H); 10.07 (bs, 1H). MS(LSIMS): 593[M+HI]$^+$.

EXAMPLE 6

1-Acetyl-2-(4-{2-[3-methoxy-4-(3-o-tolyl-ureido)-phenyl]-acetylamino{-phenyl)-pyrrolidine-3-carboxylic Acid A stirred solution 1-acetyl-2-(4-{2-[3-methoxy-4-(3-o-tolyl-ureido)-phenyl]-acetylamino}-phenyl)-pyrrolidine-3-carboxylic acid ethyl ester (2.2 g, Reference Example 18) in ethanol (100 mL) was treated dropwise with aqueous sodium hydroxide solution (5.7 mL, 1M). After stirring at room temperature for 20 hours the mixture was evaporated 40° C. under reduced pressure (2.7 kPa). The residue was treated with water (300 mL) and this mixture was washed with ethyl acetate (50 mL). The pH of the aqueous phase was adjusted to 2 by addition of hydrochloric acid (6.5 mL, 1M). The resulting white solid was centrifuged (3000 rpm for 5 minutes) then dried under reduced pressure to afford the title compound (1.56 g) as a white solid, m.p. 204° C.

$^1$H-NMR [250 MHz, (CD$_3$)$_2$SO]: δ 1.60 to 2.20 (very broad band, 3H); 2.13 (m, 2H); 2.29 (s, 3H); 2.89 (m, 1H);

3.60 (s, 2H); 3.72 (m, 2H); 3.91 (s, 3H); 5.19 (bs, 1H); 6.88 (dd, J=8 and 2 Hz, 1H); 6.97 (dt, J=7.5 and 1 Hz, 1H); 7.03 (d, J=2 Hz, 1H); 7.10 to 7.25 (m, 4H); 7.57 (very bd, J=7.5 Hz, 2H); 7.72 (bd, J=7.5 Hz, 1H); 8.01 (d, J=8 Hz, 1H); 8.29 (bs, 1H); 8.32 (bs, 1H); 9.76 (bs, 1H). MS(ES): 567(M+Na$^+$).

EXAMPLE 7

(−)1-Benzoyl-4-(4-{2-[3-methoxy-4-(3-o-tolyl-ureido)-phenyl]-acetylamino}-phenyl)-pyrrolidine-3-carboxylic Acid A solution of N-{4-[1-benzoyl-4-(10, 10-dimethyl-3,3-dioxo-31 6-thia-4-aza-tricyclo[5.2.1.0 1,5]decane-4-carbonyl)-pyrrolidin-3-yl]-phenyl}-2-[3-methoxy-4-(3-o-tolyl-ureido)-phenyl]-acetamide (0.187 g, Reference Example 21, diastereoisomer B) in a mixture of tetrahydrofuran (3 mL) and methanol (4 mL), at 23° C., was treated with aqueous sodium hydroxide solution (0.4 mL, 1M). After stirring at 23° C. for 20 hours the reaction mixture was concentrated to remove the organic solvents. The remaining aqueous solution was washed twice with ethyl acetate (25 mL) then cooled at 5° C. and then treated with concentrated hydrochloric acid (0.5 mL). After stirring at 23° C. for 3 hours the white precipitate was filtered and subjected to reverse phase chromatography [3 successive injections of 0.5 mL mother solution prepared from 150 mg crude sample and 1.6 mL acetonitrile filtered through a 200 μ filter; Column UP3 ODB.10M, Uptisphere, C-18, 3 μ ODB, 10 mm ID×100 mm L (Interchim, Montlucon, France); gradient elution conditions using mixtures of acetonitrile and water, 0–10 minutes 93:3, 11–20 minutes ramp up to 57: 43, next 15 minutes 57: 43; flow rate 3 mL/minute; UV detection at 254 nm.] Fractions containing the compound with R$_F$ 17/53 (RP-TLC C18 Merck, #1.15685, Darmstadt, Germany, acetonitrile:water, 50:50, v/v) were pooled and concentrated under reduced pressure (2.7 kPa) to give the title compound (53 mg) as a white solid. $^1$H-NMR [400 MHz, (CD$_3$)$_2$SO], a mixture of rotamers at ambient temperature ]: δ 2.26 (s, 3H); 3.20 to 3.40 (m, 1H); 3.45 to 3.60 (m, 2H); 3.57 and 3.59 (2 s, all of 2H); 3.72 (m, 2H); 3.89 and 3.90 (2 s, all of 3H); 3.90 to 4.05 (m, 1H); 6.85 (m, 1H); 6.95 (bt, J=7.5 Hz, 1H); 7.01 and 7.03 (2 bs, all of 1H); 7.10 to 7.20 (m, 2H); 7.24 (d, J=8 Hz, 1H); 7.30 (bd, J=8 Hz, 1H); 7.40 to 7.60 (m, 7H); 7.80 (d, J=8 Hz, 1H); 8.00 to 8.10 (m, 1H); 8.48 (bs, 1H); 8.59 (bs, 1H); 10.08 and 10.11 (2 bs, all of 1H); 12.40 to 12.80 (very bs, 1H). MS(LSIMS): 607[M+H]$^+$. [α]$^D$-41.1 (c=0.51, dimethylsulphoxide).

EXAMPLE 8

4-(4-{2-[3-Methoxy-4-(3-o-tolyl-ureido)-phenyl-acetylamino}-phenyl)-pyrrolidine-3-carboxylic Acid A solution of 1-benzyl-4-(4-{2-[3-methoxy-4-(3-o-tolyl-ureido)-phenyl]-acetylamino}-phenyl)-pyrrolidine-3-carboxylic acid (0.4 g, Example 5) in acetic acid (10 mL) was hydrogenated under 30 bar at 20° C. in the presence of palladium dihydroxide (0.4 g) for 20 hours. The reaction mixture was filtered through a celite pad and the pad was washed with acetic acid. The combined filtrate plus washings were evaporated and the residual orange oil was stirred with ethyl acetate (50 mL) for 20 hours then filtered to give the title compound (0.21 g) as a white powder, m.p. 218° C. $^1$H-NMR [500 MHz, (CD$_3$)$_2$SO plus a few drops of CD$_3$COOD, 383° K.: δ 1.89 (broad band, 1H); 2.26 (s, 3H); 3.16 (very broad band, 2H); 3.50 to 3.70 (very broad band, 3H); 3.60 (s, 2H); 3.89 (s, 3H); 6.86 (bd, J=8 Hz, 1H); 6.95 (bt, J=7.5 Hz, 1H); 7.01 (bs, 1H); 7.05 to 7.20 (m, 2H); 7.27 (bd, J=8 Hz, 2H); 7.56 (bd, J=8 Hz, 2H); 7.72 (bd, J=8 Hz, 1H); 8.01 (d, J=8 Hz, 1H). MS(LSIMS): 503[M+H]$^+$.

REFERENCE EXAMPLE 1

1-Acetyl-4-(4-{2-[3-methoxy-4-(3-o-tolyl-ureido)-phenal]-acetylamino}-phenyl)-pyrrolidine-3-carboxylic Acid Ethyl Ester.

A stirred solution of [3-methoxy-4-(3-o-tolyl-ureido)-phenyl]-acetic acid (1.63 g, prepared as described in Example 52B of International Patent Application Publication No. WO 96/22966) in anhydrous tetrahydrofuran (80 ml), at 23° C. and under an atmosphere of argon, was treated with benzotriazol-lyloxytris(dimethylamino)phosphonium hexafluorophosphate (2.3 g). After stirring for 1 hour the mixture was treated with 1-acetyl-4-(4-amino-phenyl)-pyrrolidine-3-carboxylic acid ethyl ester (1.43 g, Reference Example 2) then with triethylamine (2.92 ml) and dimethylaminopyridine (0.1 g). The resulting mixture was stirred at 23° C. for a further 20 hours then evaporated (40° C. and 2.7 kPa). The residue was treated with ethyl acetate (200 ml) and the resulting solution was washed twice with water (100 ml), then with brine (100 ml), then with water, then dried over magnesium sulphate and then evaporated under reduced pressure (40° C., 2.7 kPa). The residual white meringue was triturated with diethyl ether (50 ml) for 20 hours and the insoluble material was subjected to chromatography on silica (500 g, 0.045–0.020 mm particle size, 60 mm internal diameter stainless steel column) eluting at 100 ml per minute with a mixture of dichloromethane and methanol (95:5, v/v) affording the title compound (1.62 g) as a white foamy solid. TLC: R$_F$=50/74 [on silica eluting with a mixture of dichloromethane and methanol (95:5, v/v)]. $^1$H-NMR [400 MHz, (CD$_3$)$_2$SO]: δ 1.00 to 1.15 (m, 3H); 1.96 and 1.99 (2 s, 3H); 2.26 (s, 3H); 3.15 to 3.70 and 3.80 to 4.00 (2 m, 6H); 3.58 (s, 2H); 3.90 (s, 3H); 4.02 (m, 2H); 6.86 (dd, J=8 and 1.5 Hz, 1H); 6.95 (bt, J=7.5 Hz, 1H); 7.02 (d, J=1.5 Hz, 1H); 7.10 to 7.20 (m, 2H); 7.27 (m, 2H); 7.56 (m, 2H); 7.81 (d, J=7.5 Hz, 1H); 8.05 (d, J=8 Hz, 1H); 8.48 (s, 1H); 8.59 (s, 1H); 10.12 and 10.13 (2 s, 1H). MS [DCI (reactant gas, ammonia)]: 573[M+H]$^+$.

REFERENCE EXAMPLE 2

1-Acelyl-4-(4-amino-phenyl)-pyrrolidine-3-carboxylic Acid Ethyl Ester

A stirred solution of 1-acetyl-4-(4-nitro-phenyl)-pyrrolidine-3-carboxylic acid ethyl ester (1.82 g, Reference Example 3) in ethyl acetate (69 ml) was treated portionwise with tin chloride (6.7 g) then the mixture was heated to 70° C. After 8 hours, the mixture was cooled to 25° C. and then treated with ice-water (300 ml). The pH of the mixture was adjusted to 9 by addition of a freshly prepared aqueous sodium bicarbonate solution (5%), affording a white suspension which was filtered through a pad of celite. The filtrate was separated and the aqueous layer was extracted twice with ethyl acetate (50 ml) and the combined organics were dried over magnesium sulphate then evaporated (40° C. and 2.7 kPa) affording the title compound (1.58 g) as an orange oil which was used without further purification. TLC: R$_F$=54/85 [on silica plates eluting with a mixture of dichloromethane and methanol (90:10, v/v)]. $^1$H-NMR [400 MHz, (CD$_3$)$_2$SO]: δ 1.00 to 1.15 (m, 3H); 1.95 and 1.97 (2 s, 3H); 3.05 to 3.95 (m, 6H); 4.02 (m, 2H); 4.97 and 4.99 (2 bs, 2H); 6.52 (m, 2H); 6.94 and 6.98 (2 d, J=8.5 Hz, 2H). MS [EI]: 276[M]$^+$.

REFERENCE EXAMPLE 3

1-Acetyl-4-(4-nitro-phenyl)-pyrrolidine-3-carboxylic Acid Ethyl Ester

A stirred solution of 4-(4-nitro-phenyl)-pyrrolidine-3-carboxylic acid ethyl ester (2 g, Reference Example 4) in dry dichloromethane (40 ml) was treated with triethylamine (1.21 ml) at 23° C. After stirring for 5 minutes the mixture was treated dropwise with a solution of acetyl chloride (0.62 ml) in dichloromethane (3 ml) and after stirring for a further 2 hours the mixture was then treated with triethylamine (1 ml). Stirring was continued for 15 minutes then the reaction mixture was treated with water (100 ml). The organic phase was separated then washed with hydrochloric acid (50 ml, 1N), then with water (50 ml), then dried over magnesium sulphate and then evaporated (40° C. and 2.7 kPa) affording the title compound (1.82 g) as a brown oil. TLC: $R_F$=65/80 [on silica plates eluting with a mixture of dichloromethane and methanol (90/10, v/v)]. $^1$H-NMR (300 MHz, CDCl$_3$): δ 1.05 to 1.25 (m, 3H); 2.08 and 2.10 (2 s, 3H); 3.24 (m, 1H); 3.45 to 4.20 (m, 5H); 4.10 (m, 2H); 7.43 (m, 2H); 8.20 (m, 2H). MS (EI): 306[M]$^+$.

REFERENCE EXAMPLE 4

4-(4-Nitro-phenyl)-pyrrolidine-3-carboxylic Acid Ethyl Ester

A stirred solution of 4-(4-nitro-phenyl)-pyrrolidine-1,3-dicarboxylic acid 3-ethyl ester 1-vinyl ester (6 g, Reference Example 5) in dioxane (30 ml), at 25° C., was treated dropwise with hydrochloric acid (15 ml, 4N). After stirring for 2 hours the mixture was treated with a further aliquot of hydrochloric acid (15 ml, 4N) and stirring was continued at 25° C. for a further 2 hours. The reaction mixture was evaporated (40° C. and 2.7 kPa) and the residue was heated at reflux temperature with ethanol (30 ml) for 45 minutes. The mixture was cooled to room temperature then evaporated and the residue was triturated with diethyl ether (100 ml) for 20 hours affording the title compound (4.3 g) as a white solid. TLC: $R_F$=25/70 [on silica plates eluting with a mixture of dichloromethane and methanol, (90:10, v/v)]. $^1$H-NMR [400 MHz, (CD$_3$)$_2$SO]: δ 1.09 (t, J=7 Hz, 3H); 3.25 to 3.85 (3 m, 6H); 4.05 (m, 2H); 7.76 (d, J=8.5 Hz, 2H); 8.24 (d, J=8.5 Hz, 2H); 9.90 (b, 2H). MS (EI): 264[M]$^+$.

REFERENCE EXAMPLE 5

4-(4-Nitro-phenyl)-pyrrolidine-1,3-dicarboxylic acid 3-ethyl ester 1-vinyl Ester A stirred solution of 1-benzyl-4-(4-nitro-phenyl)-pyrrolidine-3-carboxylic acid ethyl ester (9.56 g, Reference Example 6) in 1,2-dichloroethane (25 ml), at 25° C. and under an atmosphere of argon, was treated dropwise with vinyl chloroformate (2.5 ml). The resulting mixture was heated at reflux for 20 hours then evaporated (40° C. and 2.7 kPa). The residue was subjected to flash chromatography on silica (0.045–0.020 mm particle size) eluting with a mixture of cyclohexane and ethyl acetate (50:50, v/v) affording the title compound (8.38 g) as a white solid. $^1$H-NMR [500 MHz, (CD$_3$)$_2$SO]: δ 1.07 (m, 3H); 3.35 to 3.70 and 3.70 to 4.00 (2 m, 6H); 4.03 (m, 2H); 4.54 and 4.56 (2 d, J=6 Hz, 1H); 4.79 and 4.85 (2 d, J=14 Hz, 1H); 7.16 (dd, J=14 and 6 Hz, 1H); 7.69 (d, J=8 Hz, 2H); 8.23 (d, J=8 Hz, 2H). MS (EI): 334 [M]$^+$.

REFERENCE EXAMPLE 6

1-Benzyl-4-(4-nitro-phenyl)-pyrrolidine-3-carboxylic Acid Ethyl Ester

A stirred solution of 4-nitroethylcinamate (10 g) in dichloromethane (200 ml), at 23° C., was treated with N-(butoxymethyl)-N-(trimethylsilylmethyl)benzylamine (10 g, prepared as described in Tetrahedron Letters, 1996, 37(43), page 7743–7744) followed immediately by treatment with trifluoroacetic acid (0.25 ml). After stirring at 25° for 20 hours a further aliquot of trifluoroacetic acid (0.5 ml) was added and stirring was continued for a further 20 hours. The reaction mixture was cooled to 5° C., then treated with sodium carbonate (5 g) and then filtered. The filtrate was concentrated under reduced pressure (40° C. and 2.7 kPa) and then treated with anhydrous ethanol (250 ml) followed by oxalic acid (4 g). The mixture was triturated for 10 minutes then stood at 25° C. for 20 hours. The resulting white crystalline solid was filtered then washed twice with ethanol (10 ml), then dried, then treated water (600 ml). The pH of the mixture was adjusted to 6–7 by addition of potassium bicarbonate (10 g) during 30 minutes then extracted with ethyl acetate (400 ml). The organic extract was dried over magnesium sulphate then evaporated (40° C. and 2.7 kPa) affording the title compound (9.36 g) as an orange oil.

$^1$H-NMR [400 MHz, (CD$_3$)$_2$SO]: δ 1.14 (t, J=7 Hz, 3H); 2.63 (m, 1H); 2.85 (m, 1H); 2.99 (m, 2H); 3.14 (m, 1H); 3.66 (AB system, J=13 Hz, 2H); 3.65 to 3.80 (m, 1H); 4.07 (m, 2H); 7.20 to 7.40 (m, 5H); 7.63 (d, J=8.5 Hz, 2H); 8.18 (d, J=8.5 Hz, 2H). MS (EI): 354[M]$^+$.

REFERENCE EXAMPLE 7

1-Benzoyl-4-(4-{2-[3-methoxy-4-(3-o-tolyl-ureido)-phenyl]-acetylamino}-phenyl)-pyrrolidine-3-carboxylic Acid Ethyl Ester A stirred solution of [3-methoxy-4-(3-o-tolyl-ureido)-phenyl]-acetic acid (5.1 g) in anhydrous tetrahydrofuran (140 ml), at 23° C. and under an atmosphere of argon, was treated with benzotriazol-1yloxytris(dimethylamino) phosphonium hexafluorophosphate (8.61 g). After stirring for 1 hour the mixture was treated with 1-benzoyl-4-(4-amino-phenyl)-pyrrolidine-3-carboxylic acid ethyl ester (5.48 g, Reference Example 8) then with triethylamine (9.1 ml), dimethylaminopyridine (0.2 g) and dimethylformamide (5 ml). The resulting mixture was stirred at 23° C. for 2 days then evaporated (40° C. and 2.7 kPa). The residue was treated with ethyl acetate (300 ml) and the resulting solution was washed twice with water (200 ml), twice with hydrochloric acid (200 ml, 1N), then twice with aqueous sodium bicarbonate solution (200 ml, 10%), then with brine (100 ml), then with water (100 ml), then dried over magnesium sulphate and then evaporated (40° C. and 2.7 kPa). The resulting white meringue was triturated with diethyl ether (50 ml) for 20 hours affording the title compound (9.6 g) as a white powder, m.p. 130° C. $^1$H-NMR [500 MHz, (CD$_3$)$_2$SO at 383° K.]: δ 1.15 (t, J=7 Hz, 3H); 2.30 (s, 3H); 3.33 (m, 1H); 3.50 to 3.70 (m, 2H); 3.62 (s, 2H); 3.77 (m, 1H); 3.85 to 4.00 (m, 2H); 3.91 (s, 3H); 4.10 (q, J=7 Hz, 2H); 6.89 (bd, J=8 Hz, 1H); 6.95 to 7.05 (m, 1H); 7.04 (d, J=2 Hz, 1H); 7.15 (t, J=8 Hz, 1H); 7.20 (d, J=7.5 Hz, 1H); 7.25 (d, J=8 Hz, 2H); 7.45 (m, 3H); 7.54 (m, 4H); 7.69 (d, J=8 Hz, 1H); 8.01 (d, J=8 Hz, 1H); 8.16 (s, 1H); 8.22 (s, 1H); 9.56 (s, 1H). MS [DCI (reactant gas, ammonia)]: 635[M+H]$^+$.

REFERENCE EXAMPLE 8

4-(4-Amino-phenyl)-1-benzoyl-pyrrolidine-3-carboxylic Acid Ethyl Ester

A stirred solution of 1-benzoyl-4-(4-nitro-phenyl)-pyrrolidine-3-carboxylic acid ethyl ester (10 g, Reference Example 9) in a mixture of ethyl acetate (324 ml) and ethanol (78 ml), at 24° C., was treated portionwise with tin chloride (30.65 g) then heated at 80° C. for 4 hours. After cooling to 24° C. the mixture was treated with water (400 ml), then with aqueous sodium bicarbonate solution (125 ml, 5%) and then filtered through a pad of celite washing twice with ethyl acetate (300 ml). The aqueous layer from the filtrate was separated and extracted twice with ethyl acetate (300 ml). The combined organic phases were dried over magnesium sulphate and evaporated (40° C. and 2.7 kPa). The residue was triturated with diethyl ether (100 ml)

affording the title compound (5.48 g) as a white powder. $^1$H-NMR [250 MHz, (CD$_3$)$_2$SO at 373° K.]: δ 1.14 (t, J=7 Hz, 3H); 3.24 (m, 1H); 3.40 to 3.60 (m, 2H); 3.73 (dd, J=11 and 8.5 Hz, 1H); 3.80 to 4.00 (m, 2H); 4.08 (q, J=7 Hz, 2H); 6.58 (d, J=8 Hz, 2H); 6.98 (d, J=8 Hz, 2H); 7.40 to 7.60 (m, 5H).

MS (EI): 338[M]$^+$.

REFERENCE EXAMPLE 9
1-Benzoyl-4-(4-nitro-phenyl)-pyrrolidine-3-carboxylic Acid Ethyl Ester A stirred solution of 4-(4-nitro-phenyl)-pyrrolidine-3-carboxylic acid ethyl ester (7.5 g, Reference Example 4) in methylene chloride (100 ml), at 23° C., was treated dropwise with triethylamine (5.8 ml). After stirring for 15 minutes the mixture was treated dropwise with a solution of benzoyl chloride [prepared in a separate vessel by treating a stirred solution of benzoic acid (5 g) in methylene chloride (15 ml), at 23° C., with oxalyl chloride (5 ml) and after stirring for 2 hours evaporating the reaction mixture] in methylene chloride (3.5 ml). The resulting dark brown mixture was stirred for 1.5 hours at 23° C. then filtered. The filtrate was successively washed with water (100 ml), then twice with hydrochloric acid (100 ml, 1N), then with brine (100 ml), then water (100 ml), then dried over magnesium sulphate and then evaporated (40° C. and 2.7 kPa) affording the title compound (10 g) as a viscous oil. $^1$H-NMR [400 MHz, (CD$_3$)$_2$SO at 383° K.] δ 1.13 (t, J=7 Hz, 3H); 3.49 (m, 1H); 3.65 (m, 1H); 3.75 to 3.90 (m, 2H); 3.90 to 4.20 (m, 2H); 4.09 (m, 2H);7.40 to 7.65 (m, 5H); 7.66 (d, J=8.5 Hz, 2H); 8.19 (d, J=8.5 Hz, 2H). MS [DCI (reactant gas, ammonia)]: 369[M+H]$^+$, 386[M+NH$_4$]$^+$.

REFERENCE EXAMPLE 10
1-(3-Ethoxycarbonyl-propionyl)4-(4-2-[3-methoxy-4-(3-o-tolyl-ureido)-phenyl]-acetylamino}-phenyl)-pyrrolidine-3-carboxylic Acid Ethyl Ester A stirred solution of [3-methoxy-4-(3-o-tolyl-ureido)-phenyl]-acetic acid (0.189 g, prepared as described in Example 52B of International Patent Application Publication No. WO 96/22966) in anhydrous tetrahydrofuran (5 ml), at 20° C. and under an atmosphere of argon, was treated with benzotriazol-lyloxytris(dimethylamino)phosphonium hexafluorophosphate (0.318 g). After 20 minutes the mixture was then treated with 4-(4-amino-phenyl)-1-(3-ethoxycarbonyl-propionyl)-pyrrolidine-3-carboxylic acid ethyl ester(5.48 g, Reference Example 11) followed by triethylamine (0.34 ml) and dimethylaminopyridine (0.007 g). The resulting mixture was stirred at 20° C. for 20 hours then evaporated (40° C. and 2.7 kPa). The residue was treated with ethyl acetate (50 ml) and the resulting solution was washed with water (50 ml), then with citric acid (50 ml, 1N), then with aqueous sodium bicarbonate solution (50 ml, 10%), then with brine (50 ml) then with water (50 ml), then dried over magnesium sulphate and then evaporated (40° C. and 2.7 kPa) affording the title compound (0.3 g) as an off-white powder. TLC: R$_F$=33/66 [on silica plates eluting with a mixture of dichloromethane and methanol (90:10, v/v)]. $^1$H-NMR [250 MHz, (CD$_3$)$_2$SO at 373° K.]: δ 1.13 (t, J=7 Hz, 3H); 1.21 (t, J=7 Hz, 3H); 2.29 (s, 3H); 2.55 (bs, 4H); 3.20 to 3.75 (b, 4H); 3.60 (s, 2H); 3.80 to 4.10 (b, 2H); 3.90 (s, 3H); 4.09 (m, 4H); 6.87 (dd, J=8.5 and 2 Hz, 1H); 6.98 (t, J=7.5 Hz, 1H); 7.03 (d, J=2 Hz, 1H); from 7.10 to 7.25 (m, 2H); 7.25 (d, J=8.5 Hz, 2H); 7.56 (d, J=8.5 Hz, 2H); 7.71 (d, J=8 Hz, 1H); 8.02 (d, J=8.5 Hz, 1H); 8.28 (bs, 1H); 8.31 (bs, 1H); 9.74 (bs, 1H). MS (ES): 681[M+Na]$^+$.

REFERENCE EXAMPLE 11
4-(4-Amino-phenyl)-1-(3-ethoxycarbonyl-propionyl) pyrrolidine-3-carboxylic Acid Ethyl Ester A solution of 1-(3-ethoxycarbonyl-propionyl)-4-(4-nitro-phenyl)-pyrrolidine-3-carboxylic acid ethyl ester (0.33 g, Reference Example 12) in acetic acid (5 ml) and 10% palladium on charcoal (0.1 g) was stirred under a hydrogen atmosphere (1 bar) for 20 hours then filtered through a pad of celite. The filtrate was evaporated (40° C. and 2.7 kPa) affording the title compound (0.218 g) as an oil. MS [DCI (reactant gas, ammonia)]: 363 [M+H]$^+$.

REFERENCE EXAMPLE 12
1-(3-Ethoxycarbonyl-propionyl)-4-(4-nitro-phenyl)-pyrrolidine-3-carboxylic Acid Ethyl Ester A stirred mixture of 4-(4-nitro-phenyl)-pyrrolidine-3-carboxylic acid ethyl ester (0.3 g, Reference Example 4) and triethylamine (0.42 ml) in dichloromethane (6 ml), at 20° C., was treated dropwise with ethyl succinyl chloride (0.18 g). After stirring for 20 hours the solution was washed twice with water (50 m]), then twice with brine (50 ml), then with water (50 ml), then dried over magnesium sulphate and then evaporated (40° C. and 2.7 kPa) affording the title compound (0.3 g) as a light brown oil. TLC: R$_F$=51/81 [on silica plates eluting with a mixture of dichloromethane and methanol (90: 10, v/v)]. MS [DCI (reactant gas, ammonia)]: 393[M+H]$^+$.

REFERENCE EXAMPLE 13
1-Benzoyl-2-(4-{2-[3-methoxy-4-(3-o-tolyl-ureido)-phenyl]-acetylamino}-phenyl)-pyrrolidine-3-carboxylic Acid Ethyl Ester A stirred solution of [3-methoxy-4-(3-o-tolyl-ureido)-phenyl]-acetic acid (1.35 g, prepared as described in Example 52B of International Patent Application Publication No. WO 96/22966) in anhydrous tetrahydrofuran (60 ml), at 20° C. and under an atmosphere of argon, was treated with benzotriazol-lyloxytris(dimethylamino)phosphonium hexafluorophosphate (2.04 g). After stirring for 10 minutes the mixture was treated with 2-(4-amino-phenyl)-1-benzoyl-pyrrolidine-3-carboxylic acid methyl ester (1.5 g, Reference Example 14) then with triethylamine (1.77 ml) and dimethylaminopyridine (0.051 g). The resulting mixture was stirred at 20° C. for 60 hours then evaporated (40° C. and 2.7 kPa). The residue was dissolved in ethyl acetate (150 ml) and the solution was washed with water (100 ml), then with aqueous potassium bicarbonate solution (100 ml, 10%), then with water (50 ml), then dried over magnesium sulphate and then evaporated under reduced pressure (40° C., 2.7 kPa). The residue was subjected to flash chromatography on silica (200 g, 0.045–0.020 mm particle size) eluting with a mixture of cyclohexane and ethyl acetate (30:70, v/v) affording the title compound (0.33 g) as an off-white powder. MS [DCI (reactant gas, ammonia)]: 621 [M+H]$^+$.

REFERENCE EXAMPLE 14
2-(4-Amino-phenyl)-1-benzoyl-pyrrolidine-3-carboxylic acid methyl and 2-(4-Amino-phenyl-1-benzoyl-pyrrolidine-3-carboxylic Acid Ethyl Ester A stirred solution of 1-benzoyl-2-(4-nitro-phenyl)-pyrrolidine-3-carboxylic acid methyl ester (8.3 g, Reference Example 15) in a mixture of ethanol (150 ml) and hydrochloric acid (117 ml, 3N), at reflux temperature, was treated with tin shots (8.3 g). After 1 hour the mixture was cooled to 20° C., then treated with water (300 ml) and then the pH of the mixture was adjusted to 8 by addition of potassium bicarbonate (10 g). The mixture was triturated with ethyl acetate (300 ml) and filtered through a pad of celite. The aqueous layer from the filtrate was separated and extracted twice with ethyl acetate (300 ml). The combined organic extracts were dried over magnesium sulphate and evaporated (40° C. and 2.7 kPa). The residue was subjected to chromatography on silica (500 g, 0.020–0.045 mm particle size) using a 60 mm internal diameter column and eluting with a mixture of dichloromethane and methanol (98:2, v/v) at 120 ml/minute affording the title compounds (2.64 g) in a ratio of ⅓ methyl ester to ⅔ ethyl ester as determined by NMR spectroscopy. $^1$H-NMR [300 MHz, $(CD_3)_2SO$ at 383° K.]: δ 1.04 (t, J=7 Hz, 2H); 2.00 to 2.45 (m, 2H); 3.39 (s, 1H); 3.40 to 4.00 (m, all 3H); 3.80 to 4.00 (m, 1.3H); 4.64 (b, 2H); 5.18 (m, 1H); 6.51 (m, 2H); 6.75 (m, 2H); 7.20 to 7.45 (m, 5H). MS (EI): 338 [M]$^+$ (ethyl ester); 324 [M]$^+$ (methyl ester).

REFERENCE EXAMPLE 15

1-Benzoyl-2-(4-nitro-phenyl)-pyrrolidine-3-carboxylic Acid Methyl Ester

A stirred solution of (4-nitro-benzylidene)-trimethylsilanylmethyl-amine (22 g, prepared as described in Chem. Pharm. Bull. 31(11) page 3939, 1893) in tetrahydrofuran (440 ml), at 45° C., was treated dropwise over 1.5 hour with a mixture of benzoyl chloride (10.1 ml) and methyl acrylate (9.3 ml) in tetrahydrofuran (500 ml). After stirring for 2.5 hours at 45° C. the mixture was allowed to cool to 20° C. then evaporated (40° C. and 2.7 kPa). The residue was dissolved in ethyl acetate (800 ml) and the solution was washed with hydrochloric acid (500 ml, 1N), then with aqueous sodium hydroxide solution (500 ml, 1N), then with water (500 ml), then dried over magnesium sulphate and then evaporated (40° C. and 2.7 kPa). The residue was subjected to chromatography on silica (500 g, 0.020–0.045 mm particle size) using a 60 mm internal diameter column and eluting with a mixture of cyclohexane and ethyl acetate (80:20, v/v) at 100 ml/minute affording the title compound (8.33 g) as a yellowish powder. $^1$H-NMR [500 MHz, $(CD_3)_2SO$ at 373° K.] δ 2.19 (m, 1H); 2.32 (m, 1H); 3.34 (s, 3H); 3.70 (m, 2H); 4.03 (m, 1H); 5.52 (m, 1H); 7.35 to 7.50 (m, 7H); 8.12 (d, J=8.5 Hz, 2H). MS (EI): 354[M]$^+$.

REFERENCE EXAMPLE 16

1-Benzyl-4-(4-{2-[3-methoxy-4-(3-o-tolyl-ureido)-phenyl]-acetylamino}-phenyl)-pyrrolidine-3-20b carboxylic Acid Ethyl Ester A stirred solution of 1-benzyl-4-(4-amino-phenyl)-pyrrolidine-3-carboxylic acid ethyl ester (2.27 g, Reference Example 17), 3-methoxy-4-(3-o-tolyl-ureido)-phenyl]-acetic acid (2.20 g) and benzotriazolyl-N-oxy-tris (dimethylamino)phosphonium hexafluorophosphate (3.09 g) was treated with a mixture of triethyl amine (3.58 mL) and 4-dimethyl aminopyridine (85.5 mg) in tetrahydrofuran (20 mL). After stirring overnight at room temperature the reaction mixture was diluted with ethyl acetate (200 mL), then washed with water (200 mL) and then washed with aqueous sodium hydrogen carbonate solution (200 mL, 10%). The organic phase was dried over magnesium sulfate and then concentrated under reduced pressure (2.7 kPa). The residue was subjected to chromatography on silica (500 g, 20–45 μm) eluting with a mixture of cyclohexane and ethyl acetate (70:30, v/v). Fractions containing the compound with $R_F$=80/124 (thin layer chromatography plate ref. # 05719, Merck KGaA, 64271 Darmstadt, Germany, 70:30, cyclohexane:ethyl acetate, v/v) were pooled and concentrated under reduced pressure (2.7 kPa), to give the title compound (2.95 g) as an off-white powder.

REFERENCE EXAMPLE 17

1-Benzyl-4-(4-amino-phenyl)-pyrrolidine-3-carboxylic Acid Ethyl Ester

A mixture of 1-benzyl-4-(4-nitro-phenyl)-pyrrolidine-3-carboxylic acid ethyl ester (15 g, Reference Example 6), tin (25.12 g), hydrochloric acid (230 mL, 3M) and ethanol (230 mL) was heated at reflux temperature for 1 hour. After cooling to room temperature the pH of the mixture was adjusted to 9 by addition of solid sodium carbonate. The mixture was then diluted with water to give a final volume of 1000 mL and then filtered through a pad of celite. The clear filtrate was extracted twice with ethyl acetate (1000 mL). The combined extracts were dried over magnesium sulfate and then evaporated. The crude residue was subjected to chromatography using a Prochrom LC60 column, 40 cm silica bed, 20–45 μm, eluting with a mixture of cyclohexane and ethyl acetate (70:30, v/v) at 100 cm$^3$/minute flow rate. The fractions containing the compound with $R_F$=60/171 (thin layer chromatography plate ref. #05719, Merck KGaA, 64271 Darmstadt, Germany, cyclohexane:ethyl acetate, 70:30, v/v) were pooled and concentrated under reduced pressure (2.7 kPa) to give the title compound (7.22 g) as a yellow oil.

REFERENCE EXAMPLE 18

1-Acetyl-2-(4-12-[3-methoxy-4-(3-o-tolyl-ureido)-phenyl]-acetylamino}-phenyl)-pyrrolidine-3-carboxylic Acid Ethyl Ester A stirred suspension of 3-methoxy-4-(3-o-tolyl-ureido)-phenyl]-acetic acid (1.73 g, prepared as described in example 52B of International patent Application Publication No. WO 96/22966) in tetrahydrofuran (60 mL) was treated with benzotriazolyl-N-oxy-tris(dimethylamino)-phosphonium hexafluorophosphate (2.7 g), then with 4-dimethylaminopyridine (73 mg), then with triethyl amine (3.1 mL) and then with 1-acetyl-2-(4-amino-phenyl)-pyrrolidine-3-carboxylic acid ethyl ester (1.7 g, Reference Example 19). After stirring overnight at room temperature the reaction mixture was diluted with water (100 ml) then extracted three times with ethyl acetate (100 mL). The organic extracts were dried over magnesium sulfate and then evaporated. The residue was subjected to flash chromatography on silica (20–45 μm) eluting with a mixture of dichloromethane and methanol (95:5, v/v). The fractions containing the compound of $R_F$ 32/144 (thin layer chromatography plate ref. #05719, Merck KGaA, 64271 Darmstadt, Germany, elutant dichloromethane: methanol, 95:5, v/v.) were pooled and concentrated to dryness under reduced pressure (2.7 kPa) affording the title compound (2.2 g) as a white powder.

REFERENCE EXAMPLE 19

1-Acetyl-2-(4-amino-phenyl)-pyrrolidine-3-carboxylic Acid Ethyl Ester

A stirred mixture of 1-acetyl-2-(4-nitro-phenyl)-pyrrolidine-3-carboxylic acid ethyl ester (3 g, Reference Example 20) and 10% palladium on charcoal in ethanol (150 mL) was hydrogenated under atmospheric pressure for 4 hours at room temperature and then filtered through a celite pad. The filter pad was washed with ethanol (50 mL) and the combined filtrate plus washings were evaporated. The residue was subjected to flash chromatography on silica (330 g, 20–451 μm, 0.6 bar) eluting with a mixture of dichloromethane and methanol (95:5, v/v). The fractions containing the compound of $R_F$ 16/63 (thin layer chromatography plate ref. #05719, Merck KGaA, 64271 Darmstadt, Germany, dichloromethane:methanol, 95:5, v/v) were pooled and evaporated under reduced pressure (2.7 kPa) to give the title compound (1.71 g).

REFERENCE EXAMPLE 20

1-Acetyl-2-(4-nitro-phenyl)-pyrrolidine-3-carboxylic Acid Ethyl Ester

A stirred solution of (4-nitro-benzylidene)-trimethylsilanylmethyl-amine (3.2 g) in tetrahydrofuran (120 mL), at 40° C., was treated with a solution of acetyl chloride (1 mL) and ethyl acrylate (1.6 mL) in tetrahydrofuran (60 mL). After stirring at 40° C. for 20 hours the reaction mixture was evaporated. The residual oil was treated with ethyl acetate(300 mL) and water (100 mL) and the mixture was then stirred 1,5 for 20 hours. The organic phase was washed twice with water (100 mL), then dried and then concentrated under reduced pressure (2.7 kPa). The residue was subjected to flash chromatography on silica (700, 20–45 μm, 0.6 bar) eluting with a mixture of cyclohexane and ethyl acetate (90:10, v/v) to give the title compound (3.04 g). $R_F$=37/162, thin layer chromatography plate ref. #05719, Merck KGaA, 64271 Darmstatd, Germany.

REFERENCE EXAMPLE 21

N-{4-[1-Benzoyl-4-(10, 10-dimethyl-3,3-dioxo-31 6-thia-4-aza-tricyclo[5.2.1.0 1,5]decane-4-carbonyl)-pyrrolidin-3-yl]-phenyl}-2-[3-methoxy-4-(3-o-tolyl-ureido)-phenyl]-acetamide (diastereoisomer A) and N-{4-[1-Benzoyl-4-(10, 10-dimethyl-3, 3-dioxo-31 6-thia-4-aza-tricyclo[5.2.1.0 1,5]decane-4-carbonyl)-pyrrolidin-3-yl]-phenyl}-2-[3-methoxy-4-(3-o-tolyl-ureido)-phenyl]-acetamide (Diastereoisomer B)

A solution of racemic 1-benzoyl-4-(4-{2-[3-methoxy-4-(3-o-tolyl-ureido)-phenyl]-acetylamino}-phenyl)-pyrrolidine-3-carboxylic acid (2 g, Reference Example 22) in dimethylformamide (10 mL), at 23° C., was treated with a solution of camphor sultame (0.709 g) in dimethylformamide (10 mL), then with O-(7-azabenzotriazol-1-yl)-N,N,N',N'-tetramethyluronium hexafluorophosphate (1.3 g of), then with triethyl amine (10 mL) and then with 4-dimethylaminopyridine (50 mg). After stirring at 23° C. for 20 hours the reaction mixture was diluted with water (500 mL) and this mixture was acidification by addition of hydrochloric acid (10M). The resulting precipitate was filtered and then dried under reduced pressure (2.7 kPa) affording 2 g of crude product. A portion (0.5 g) of this material dissolved in a mixture of dichloromethane (2.5 mL) and 2-propyl alcohol (50 mL) was subjected to chromatography using a Dynamax 60-A Silica Preparative Column Module, 8μ, 21.4 ID×250 mm L, Ref #83-121-C assembled with Dynamax 60-A Silica Preparative Guard Module, 8μ, 21.4 ID×50 mm L, Ref#83-121-G, (Rainin Instrument Company, Mack Road, Box 4026, Woburn, Mass. 01888-4026) and eluting with a mixture of dichloromethane and 2-propyl alcohol (96:4, v/v) with a flow rate of 10 mL/minute and UV detection at 254 nm; whilst two other portions (0.1 g) were subjected to similar chromatography conditions but eluting with a mixture of dichloromethane and 2-propyl alcohol (98: 2, v/v) at 10 mL/minute from 0 to 40 minutes and then eluting with a mixture of dichloromethane and 2-propyl alcohol (96: 4, v/v) from 55 to 90 minutes to give:

(i) N-{4-[1-benzoyl-4-(10,10-dimethyl-3, 3-dioxo-31 6-thia-4-aza-tricyclo[5.2.1.0 1,5]decane-4-carbonyl)-pyrrolidin-3-yl]-phenyl}-2-[3-methoxy-4-(3-o-tolyl-ureido)-phenyl]-acetamide, diastereoisomer A, (0.19 g). HPLC: $R_T$=7.13 minutes (a Dynamax 60-A Silica Analytical Column Module, 81μ, 4.6×250 mm, Ref. #83-101-C assembled with Dynamax 60-A Silica Analytical Guard Module, 8μ, 4.6×50 mm, Ref #83-101-G (Rainin Instrument Company, Mack Road, Box 4026, Woburn, Mass. 01888-4026); eluting with a mixture of dichloromethane and 2-propyl alcohol (96:4, v/v); flow rate 0.5 mL/minute; UV detection at 254 nm). $^1$H-NMR [400 MHz, $(CD_3)_2SO$, 383° K.]: δ 0.96(s, 3H); 1.04 (s, 3H); 1.30 (m, 1H); 1.47 (m, 1H); 1.70 to 2.05 (m, 5H); 2.29 (s, 3H); 3.55 to 3.65 (m, 3H); 3.61 (s, 2H); 3.74 (d, J=14.5 Hz, 1H); 3.75 to 3.95 (m, 3H); 3.91 (s, 3H); 4.00 (m, 1H); 4.10 (m, 1H); 6.89 (dd, J=8 and 2 Hz, 1H); 7.00 (bt, J=8 Hz, 1H); 7.04 (d, J=1.5 Hz, 1H); 7.10 to 7.25 (m, 2H); 7.22 (d, J=8.5 Hz, 1H); 7.40 to 7.60 (m, 7H); 7.70 (bd, J=8 Hz, 1H); 8.01 (d, J=8 Hz, 1H); 8.17 (bs, 1H); 8.23 (bs, 1H); 9.57 (bs, 1H). MS(LSIMS): 804[M+H]$^+$.

(ii) N-{4-[1-benzoyl-4-(10,10-dimethyl-3,3-dioxo-31 6-thia-4-aza-tricyclo[5.2.1.0 1,5]decane-4-carbonyl)-pyrrolidin-3-yl]-phenyl}-2-[3-methoxy-4-(3-o-tolyl-ureido)-phenyl]-acetamide, diastereoisomer B, (0.187 g). HPLC: $R_T$=8.32 minutes. $^1$H NMR [400 MHz, $(CD_3)_2SO$, 383° K.]: δ 0.77 (s, 3H); 0.91 (s, 3H); 1.27 (m, 1H); 1.41 (m, 1H); 1.65 to 2.00 (m, 5H); 2.29 (s, 3H); 3.50 to 3.95 (m, 7H); 3.60 (s, 2H); 3.91 (s, 3H); 3.95 to 4.05 (m, 2H); 6.87 (dd, J=8 and 2 Hz, 1H); 6.99 (bt, J=8 Hz, 1H); 7.03 (d, J=1.5 Hz, 1H); 7.10 to 7.25 (m, 2H); 7.23 (d, J=8.5 Hz, 2H); 7.40 to 7.60 (m, 7H); 7.69 (bd, J=8 Hz, 1H); 8.00 (d, J=8 Hz, 1H); 8.18 (bs, 1H); 8.23 (bs, 1H); 9.58 (bs, 1H). MS(LSIMS): 804 [M+H]$^+$.

In vitro and in vivo Test Procedures
1. Inhibitory Effects of Compounds on VLA-4 Dependent Cell Adhesion to Fibronectin and VCAM.
1.1 Metabolic Labelling of RAMOS Cells.

RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with 400 μCi/100 mls of [$^3$H]-methionine (Amersham, UK) for 18 hours at 37° C.

1.2 96 Well Plate Preparation for Adhesion Assay.

Cytostar plates (Amersham, UK) were coated with 50 μl/well of either 3 μg/ml human soluble VCAM-1 (R&D Systems Ltd, UK) or 28.8 μg/ml human tissue Fibronectin (Sigma, UK). In control non-specific binding wells 50 μl phosphate buffered saline was added. The plates were then left to dry in an incubator at 25° C., overnight. The next day the plates were blocked with 200 μl/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 μl/well of 3.6% dimethyl sulphoxide in Pucks buffer supplemented with 5 mM manganese chloride (to activate the integrin receptor Sigma, UK) and 0.2% 2.0) BSA (Sigma, UK), was added to the appropriate control test binding and non-specific binding assay wells in the plate. 50 μl/well of the test compounds at the appropriate concentrations diluted in 3.6% dimethyl sulphoxide in Pucks buffer supplemented with 5 mM manganese chloride and 0.2% BSA, was added to the test wells.

Metabolically labelled cells were suspended at $4 \times 10^6$ cells/ml in Pucks buffer that was supplemented with manganese chloride and BSA as above. 50 μl/well of cells in 3.6% dimethyl sulphoxide in Pucks buffer and supplements was added to all plate wells.

The same procedure exists for plates coated with either VCAM-1 or fibronectin and data is determined for compound inhibition of cell binding to both substrates.
1.3 Performance of Assay and Data Analysis.

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\} \times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for $IC_{50}$s for inhibition of cell adhesion to both fibronectin and VCAM-1. Particular compounds of the invention inhibit cell adhesion to fibronectin and VCAM-1 with $IC_{50}$s in the range 100 micromolar to 1 nanomolar. Preferred compounds of the invention inhibit cell adhesion to fibronectin and VCAM-1 with $IC_{50}$s in the range 10 nanomolar to 1 nanomolar.

2. Inhibition of Antigen-Induced Airway Inflammation in the Mouse and Rat.

2.1 Sensitization of the Animals.

Rats (Brown Norway, Harland Olac, UK) are sensitized on days 0, 12 and 21 with ovalbumin (100 μg, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 μg, i.p.) administered with aluminium hydroxide adjuvant (20 mg, i.p.) in saline (0.2 ml, i.p.).

2.2 Antigen Challenge.

Rats are challenged on any one day between days 28–38, while mice are challenged on any one day between days 20–30.

The animals are challenged by exposure for 30 minutes (rats) or 1 hour (mice) to an aerosol of ovalbumin (10 g/1) generated by an ultrasonic nebulizer (deVilbiss Ultraneb, US) and passed into an exposure chamber.

2.3 Treatment Protocols.

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or 1 ml/kg, i.t.

2.4 Assessment of Airway Inflammation.

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 0.5 mm pieces. Samples (rats: 400 mg; mice: 150 mg) of homogenous lung tissue are incubated in RPMI 1640/ FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK)

2.5 Data Analysis.

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where $p<0.05$ no statistical significance existed.

What is claimed is:

1. A compound of formula (I)

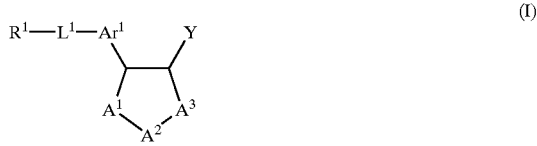

wherein:
one of $A^1$, $A^2$ and $A^3$ represents $NR^2$ and the others represent $C(R^3)(R^4)$;

$R^1$ represents $R^6N(R^7)$—C(=O)—NH—$Ar^2$—;

$R^2$ represents —(=O)—$R^8$, —C(=O)—$OR^{8a}$ or $R^{8b}$;

$R^3$ and $R^4$ each represent hydrogen or $R^8$;

$R^6$ represents hydrogen or lower alkyl and $R^7$ represents arylor arylalkyl;

$R^8$ represents alkyl, aryl, arylalkyl, cycloalkyl, cycloalkylalkyl, or alkyl substituted by an acidic functional group or a protecting group, or by —$Z^3$H, —$Z^2R^{10}$, —C(=O)—$NY^1Y^2$ or —$NY^1Y^2$;

$R^{8a}$ represents alkyl, aryl or arylalkyl;

$R^{8b}$ represents alkyl, aryl, arylalkyl or alkyl substituted by an acidic functional group or a protecting group;

$R^9$ represents aryl, cycloalkyl or cycloalkenyl;

$R^{10}$ represents alkyl, alkenyl, alkynyl, aryl, arylalkyl, arylalkenyl, arylalkynyl, cycloalkyl, cycloalkylalkyl, cycloalkenyl or cycloalkenylalkyl;

$R^{11}$ represents hydrogen or lower alkyl;

$R^{12}$ is a direct bond or an alkylene chain, an alkenylene chain or an alkynylene chain;

$R^{13}$ is —C(=O)—NH—;

$Ar^1$ represents aryldiyl;

$Ar^2$ represents aryldiyl;

$L^1$ represents a —$R^{12}$—$R^{13}$— linkage;

Y is carboxy;

$Y^1$ and $Y^2$ are independently hydrogen, alkenyl, alkyl, aryl, arylalkyl or cycloalkyl;

$Z^1$ represents NH;

$Z^2$ is O or $S(O)_n$;

$Z^3$ is O or S; and n is zero or an integer 1 or 2;

provide that in these compounds an oxygen, nitrogen or sulphur atom is not attached directly to a carbon carbon multiple bond of an alkenyl or alkynyl residue;

or a prodrug thereof, or a pharmaceutically acceptable salt or solvate thereof or prodrug.

2. A compound according to claim 1 in which $R^7$ is optionally substituted phenyl.

3. A compound according to claim 1 in which $R^6$ is hydrogen.

4. A compound according to claim 1 in which $R^6$ is hydrogen and $R^7$ is phenyl or ortho substituted phenyl.

5. A compound according to claim 4 in which $R^7$ is phenyl substituted in the ring ortho position by $C_{1-4}$ alkyl.

6. A compound according to claim 1 in which $Ar^2$ is optionally substituted phenylene.

7. A compound according to claim 6 in which $Ar^2$ is phenylene substituted by $C_{1-4}$ alkyl or $C_{1-4}$alkoxy.

8. A compound according to claim 6 in which $Ar^2$ is optionally substituted p-phenylene.

9. A compound according to claim 7 in which $Ar^2$ is p-phenylene substituted in the 3-position by $C_{1-4}$alkyl or $C_{1-4}$alkoxy.

10. A compound according to claim 1 in which $L^1$ represents a —$R^{12}$—$R^{13}$— linkage wherein $R^{12}$ represents a straight or branched $C_{1-4}$alkylene chain and $R^{13}$ represents —C(=O)—NH—.

11. A compound according to claim 10 in which $R^{12}$ represents methylene.

12. A compound according to claim 1 in which $Ar^1$ represents optionally substituted p-phenylene.

13. A compound according to claim 12 in which $Ar^1$ represents unsubstituted p-phenylene.

14. A compound according to claim 1 in which one of $A^1$, $A^2$ and $A^3$ represents $NR^2$ and the others represent $CH_2$.

15. A compound according to claim 14 in which $R^2$ is —C(=O)—$R^8$ wherein $R^8$ is as defined in claim 1.

16. A compound according to claim 15 in which $R^8$ is $C_{1-4}$alkyl or phenyl.

17. A compound according to claim 14 in which $R^2$ is aryl$C_{1-4}$alkyl.

18. A compound according to claim 17 in which $R^2$ is benzyl.

19. A compound according to claim 1 of formula (Ia):

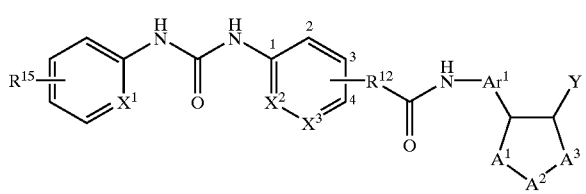

(Ia)

in which $A^1$, $A^2$, $A^3$, $R^{12}$, $Ar^1$ and Y are as defined in claim 1, $R^{15}$ is hydrogen, halogen, lower alkyl or lower alkoxy, $X^1$ represents $CR^{16}$ (where $R^{16}$ is hydrogen, lower alkyl or lower alkoxy), $X^2$ and $X^3$ independently represent $CR^{17}$ (where $R^{17}$ is hydrogen, amino, halogen, hydroxy, lower alkyl, lower alkoxy, lower alkylthio, lower alkylsulphinyl, lower alkylsulphonyl, nitro or trifluoromethyl), and the group containing $R^{12}$ is attached at the ring 3 or 4 position, or a prodrug of such compound, or a pharmaceutically acceptable salt or solvate of such compound or prodrug.

20. A compound according to claim 19 in which $R^{15}$ is hydrogen; $X^1$ represents $CR^{16}$ (where $R^{16}$ is $C_{1-4}$alkyl); $X^2$ represents $CR^{17}$ (where $R^{17}$ is $C_{1-4}$alkoxy); $X^3$ represents CH; $R^{12}$ is a straight $C_{1-4}$alkylene chain; $Ar^1$ is p-phenylene; Y represents carboxy; and the group containing $R^{12}$ is attached at the ring 4 position.

21. A compound according to claim 19 in which one of $A^1$, $A^2$ and $A^3$ represents $NR^2$ and the others represent $CH_2$.

22. A compound according to claim 21 in which $R^2$ is —C(=O)—$R^8$ wherein $R^8$ is as defined in claim 1.

23. A compound according to claim 22 in which $R^8$ is $C_{1-4}$alkyl or phenyl.

24. A compound according to claim 21 in which $R^2$ is aryl$C_{1-4}$alkyl.

25. A compound according to claim 24 in which $R^2$ is benzyl.

26. A compound according to claim 1 selected from the group consisting of:

1-acetyl-4-(4-{2-[3-methoxy-4-(3-o-tolyl-ureido)-phenyl]-acetylamino}-phenyl)-pyrrolidine-3-carboxylic acid;

1-benzoyl-4-(4-{2-[3-methoxy-4-(3-o-tolyl-ureido)-phenyl]-acetylamino}-phenyl)-pyrrolidine-3-carboxylic acid;

1-(3-carboxy-propionyl)-4-(4-{2-[3-methoxy-4-(3-o-tolyl-ureido)-phenyl]-acetylamino}-phenyl)-pyrrolidine-3-carboxylic acid;

1-benzoyl-2-(4-{2-[3-methoxy-4-(3-o-tolyl-ureido)-phenyl]-acetylamino}-phenyl)-pyrrolidine-3-carboxylic acid;

1-benzyl-4-(4-{2-[3-methoxy-4-(3-o-tolyl-ureido)-phenyl]-acetylamino}-phenyl)-pyrrolidine-3-carboxylic acid;

1-acetyl-2-(4-{2-[3-methoxy-4-(3-o-tolyl-ureido)-phenyl]-acetylamino}-phenyl)-pyrrolidine-3-carboxylic acid;

(−) 1-benzoyl-4-(4-{2-[3-methoxy-4-(3-o-tolyl-ureido)-phenyl]-acetylamino}-phenyl)-pyrrolidine-3-carboxylic acid; and 4-(4-{2-[3-methoxy-4-(3-o-tolyl-ureido)-phenyl]-acetylamino}-phenyl)-pyrrolidine-3-carboxylic acid, or a prodrug of such compound, or a pharmaceutically acceptable salt or solvate of such compound or prodrug.

27. A pharmaceutical composition comprising an effective amount of a compound according to claim 1 or a corresponding N-oxide, or a prodrug thereof or a pharmaceutically acceptable salt or solvate of such a compound or its N-oxide or a prodrug thereof, with a pharmaceutically acceptable carrier or excipient.

28. A method for the treatment of a human or non-human animal patient suffering from, or subject to, a condition which can be ameliorated by the administration of an inhibitor of α4β1 mediated cell adhesion comprising administering to said patient an effective amount of a compound according to claim 1 or a corresponding N-oxide or prodrug, or a pharmaceutically acceptable salt or solvate of such a compound or an N-oxide or prodrug thereof.

29. A method for the treatment of a patient suffering from, or subject to, asthma comprising administering to said patient an effective amount of a compound according to claim 1 or a corresponding N-oxide or prodrug, or a pharmaceutically acceptable salt or solvate of such a compound or an N-oxide or prodrug thereof.

30. A method for the treatment of a patient suffering from, or subject to, an inflammatory disease comprising administering to said patient an effective amount of a compound according to claim 1 or a corresponding N-oxide or prodrug, or a pharmaceutically acceptable salt or solvate of such a compound or an N-oxide or prodrug thereof.

31. A method for the treatment of a human or non-human animal patient suffering from, or subject to, a condition which can be ameliorated by the administration of an inhibitor of α4β1 mediated cell adhesion comprising administering to said patient an effective amount of a composition according to claim 27.

32. A method for the treatment of a patient suffering from, or subject to, asthma comprising administering to said patient an effective amount of a composition according to claim 27.

33. A method for the treatment of a patient suffering from, or subject to, an inflammatory disease comprising administering to said patient an effective amount of a composition according to claim 27.

* * * * *